(12) United States Patent
Nishida et al.

(10) Patent No.: US 11,649,433 B2
(45) Date of Patent: May 16, 2023

(54) METHOD FOR CONTROLLING DIFFERENTIATION OF PLURIPOTENT STEM CELLS

(71) Applicant: Osaka University, Osaka (JP)

(72) Inventors: Kohji Nishida, Osaka (JP); Kiyotoshi Sekiguchi, Osaka (JP); Ryuhei Hayashi, Osaka (JP); Shun Shibata, Osaka (JP)

(73) Assignee: Osaka University, Osaka (JP)

(*) Notice: Subject to any disclaimer, the term of this patent is extended or adjusted under 35 U.S.C. 154(b) by 465 days.

(21) Appl. No.: 16/482,160

(22) PCT Filed: Jan. 31, 2018

(86) PCT No.: PCT/JP2018/003315
§ 371 (c)(1),
(2) Date: Jul. 30, 2019

(87) PCT Pub. No.: WO2018/143312
PCT Pub. Date: Aug. 9, 2018

(65) Prior Publication Data
US 2020/0010800 A1      Jan. 9, 2020

(30) Foreign Application Priority Data

Jan. 31, 2017 (JP) .............................. JP2017-016302

(51) Int. Cl.
*A61K 35/545* (2015.01)
*C12N 5/079* (2010.01)
*A61K 38/18* (2006.01)

(52) U.S. Cl.
CPC .......... *C12N 5/0621* (2013.01); *A61K 35/545* (2013.01); *A61K 38/1825* (2013.01); *A61K 38/18* (2013.01); *C12N 2501/998* (2013.01); *C12N 2506/45* (2013.01); *C12N 2533/52* (2013.01)

(58) Field of Classification Search
CPC ............ C12N 5/0621; C12N 2501/998; C12N 2506/45; C12N 2533/52; A61K 35/545; A61K 38/1825; A61K 38/18
See application file for complete search history.

(56) References Cited

U.S. PATENT DOCUMENTS

| | | |
|---|---|---|
| 2004/0014665 A1 | 1/2004 | Boutaud |
| 2012/0142103 A1 | 6/2012 | Nishida et al. |
| 2012/0220031 A1 | 8/2012 | Sekiguchi |
| 2012/0225435 A1 | 9/2012 | Seger et al. |
| 2014/0127803 A1 | 5/2014 | Hayashi et al. |
| 2016/0046904 A1 | 2/2016 | Mizuguchi et al. |
| 2016/0137965 A1 | 5/2016 | Sekguchi et al. |
| 2016/0264936 A1 | 9/2016 | Nakano et al. |
| 2018/0002170 A1 | 1/2018 | Seger et al. |
| 2018/0010093 A1 | 1/2018 | Nishida et al. |

FOREIGN PATENT DOCUMENTS

| | | | |
|---|---|---|---|
| JP | WO/2011/043405 | * | 4/2011 |
| JP | 2014-513924 A | | 6/2014 |
| WO | WO 2010/134619 A1 | | 11/2010 |
| WO | WO 2012/144582 A1 | | 10/2012 |
| WO | WO 2014/168157 A1 | | 10/2014 |
| WO | WO 2014/199754 A1 | | 12/2014 |
| WO | WO 2015/068505 A1 | | 5/2015 |
| WO | WO 2016/114285 A1 | | 7/2016 |

OTHER PUBLICATIONS

Blazejewska et al., Stem Cells (2009) 27:642-652 (Year: 2009).*
Hayashi, Yohei et al., "Biological Effects of Culture Substrates on Human Pluripotent Stem Cells" Stem Cells International, 2016, pp. 1-11, vol. 2016.
Miyazaki, Takamichi et al., "Laminin E8 fragments support efficient adhesion and expansion of dissociated human pluripotent stem cells" Nature Communications, Dec. 2012, pp. 1-10, vol. 3, No. 1236.
Rowland, Teisha J. et al., "Differentiation of human pluripotent stem cells to retinal pigmented epithelium in defined conditions using purified extracellular matrix proteins" Journal of Tissue Engineering and Regenerative Medicine, 2013, pp. 642-653, vol. 7.
Shibata, Shun et al., "Selective Laminin-Directed Differentiation of Human Induced Pluripotent Stem Cells into Distinct Ocular Lineages" Cell Reports, Nov. 2018, pp. 1668-1679, vol. 25.
Supplementary Partial European Search Report for EP 18748273 dated Jan. 17, 2020.
Hayashi, Ryuhei et al., "Co-ordinated ocular development from human IPS cells and recovery of corneal function" Nature, Mar. 2016, pp. 376-380, vol. 531.
Ohta, Ryo et al., "Laminin-guided highly efficient endothelial commitment from human pluripotent stem cells" Scientific Reports, 2016, vol. 6.
Sekiguti, Kiyotoshi "Development of culture substrates for stem cells based on diversity of extracellular matrices", Regenerative Medicine, Feb. 2015, p. 142, vol. 14, Supplement.
Shibata, Shun et al., "Laminin isoforms regulate ocular development from iPS cells", Regenerative Medicine, Feb. 2017, p. 270, vol. 16, Supplement.

(Continued)

*Primary Examiner* — Stacey N MacFarlane
(74) *Attorney, Agent, or Firm* — Knobbe Martens Olson & Bear LLP

(57) ABSTRACT

The present invention relates to a method for controlling differentiation of pluripotent stem cells, which method comprises selecting a laminin or a fragment thereof based on binding affinity for the pluripotent stem cells and inducing differentiation of the pluripotent stem cells in the presence of the laminin or a fragment thereof. Here, the binding affinity for cells can be assessed by time-course observation of the survival rate and motility of the cells. According to the present invention, a cell population containing any desired proportion of differentiated cells can be produced from pluripotent stem cells in a simple manner. The cell population obtained by this production method is very useful for cell therapy-based treatment strategies for diseases.

14 Claims, 19 Drawing Sheets

(56) References Cited

OTHER PUBLICATIONS

Takayama, Kazuo et al., "Long-Term Self-Renewal of Human ES/IPS-Derived Hepatoblast-like Cells on Human Laminin 111-Coated Dishes" Stem Cell Reports, Oct. 2013, pp. 322-335, vol. 1.
Takayama Kazuo et al., "Use of laminin isoforms for differentiation of human iPS cells into hepatocytes and cholangiocytes", Program and Abstracts of the 39th Annual Meeting of the Molecular Biology Society of Japan, Nov. 2016.
Yamaguchi, Masahiro et al., "Adhesion, Migration, and Proliferation of Cultured Human Corneal Endothelial Cells by Laminin-5" IOVS, Feb. 2011, pp. 679-684, vol. 52, No. 2.
Analysis of function of basement membrane protein laminin in stem cell differentiation, Scientific research funds raising business database, https://kaken.nll.ac.jp/grant/KAKENHI-PROJECT-18770089/.
2008 Fiscal Year Annual Report on Progress in Development of Technologies for Analysis of Gene Functions etc. using Model Cells (Development of Technologies for Generation of Model Cells for Research Use), Development of Technologies for Generation of Model Cells for Research Use, NEDO Research Report Database.
International Preliminary Report on Patentability for PCT/JP2018/003315.
International Search Report for PCT/JP2018/003315 dated May 1, 2018.
Lee, Gabsang et al., "Derivation of neural crest cells from human pluripotent stem cells" Nature Protocols, 2010, pp. 688-701, vol. 5, No. 4.
Mellough, Carla B. et al., "Efficient Stage-Specific Differentiation of Human Pluripotent Stem Cells Toward Retinal Photoreceptor Cells" Stem Cells, 2012, pp. 673-686, vol. 30.
Supplementary European Search Report for EP 18748273 dated May 1, 2020.
Kaken—Research Projects "Functional analysis of basement membrane protein laminin in stem cell differentiation" Kaken Research, Apr. 2016, Abstract.
First Examination Report for Indian Application No. 201927032411 dated Feb. 15, 2022.
Substantive Examination Adverse Report for My PI2019004373 dated Mar. 11, 2022.
Office Action for VN 1-2019-04772 dated Jun. 29, 2022.
First Examination Report for AU 2018215170 dated Feb. 1, 2021 (listed in Cite No. 1).
Office Action dated Sep. 30, 2022 in corresponding Chinese Application No. 201880009619.5.

* cited by examiner

Laminin 511 coating concentration (μg/cm²)

METHOD FOR CONTROLLING DIFFERENTIATION OF PLURIPOTENT STEM CELLS

CROSS REFERENCE TO RELATED APPLICATIONS

This application is a U.S. National Phase Application of PCT International Application Number PCT/JP2018/003315, filed on Jan. 31, 2018, designating the United States of America and published in the Japanese language, which is an International Application of and claims the benefit of priority to Japanese Patent Application No. 2017-016302, filed on Jan. 31, 2017. The disclosures of the above-referenced applications are hereby expressly incorporated by reference in their entireties.

TECHNICAL FIELD

The present invention relates to a method for controlling differentiation of pluripotent stem cells. In particular, the present invention relates to a method for controlling the direction of differentiation of pluripotent stem cells to induce selective differentiation into desired ocular cell primordium and to use thereof.

BACKGROUND ART

Human pluripotent stem cells, such as human ES cells and human iPS cells, are receiving worldwide attention for their potential application to regenerative medicine. For practical application of human pluripotent stem cells to regenerative medicine, there is a need to develop techniques for inducing such stem cells to differentiate into somatic cells in a highly efficient and stable manner. Various studies are underway for developing methods for selective differentiation of human pluripotent stem cells into any desired somatic cells.

For example, in order to provide a novel therapy for serious corneal diseases such as linbal stem cell deficiency, the present inventors developed a methodology for fabricating a corneal epithelial cell sheet from iPS cells and examined the efficacy of the cell sheet in an animal model (Non Patent Literature 1). The iPS cell-derived cells obtained by the differentiation method described in Non Patent Literature 1 compose a population of various eye-related cells. For this reason, the use of such a cell population for the fabrication of corneal epithelial cell sheets requires purification of corneal epithelial cells. Non Patent Literature 1 describes purification of corneal epithelial cells by FACS sorting using antibodies against cell surface markers specific to corneal epithelial cells.

FACS sorting is a technique that allows isolation of specific cells based on cell surface antigen expression which is examined by laser irradiation to antibody-stained cells passed in a stream of fluid. This technique, however, has difficulty in ensuring the sterility of the entire flow path through which cells pass, and also has the risk of cell contamination. In addition, cells collected after FACS sorting are heavily damaged. Moreover, the maintenance of the apparatus used for FACS sorting requires special knowledge and skills. For these reasons, FACS sorting is not necessarily an ideal technique in the setting to prepare a large amount of cells used for the fabrication of corneal epithelial cell sheets for transplantation. That is, the methodology of Non Patent Literature 1 still has problems to be solved for practical and industrial use.

CITATION LIST

Non Patent Literature

Non Patent Literature 1:
Hayashi et al., Nature. 2016 Mar 17;531(7594):376-80. doi: 10.1038/nature17000. Epub 2016 Mar. 9.

SUMMARY OF INVENTION

Technical Problem

The present invention relates to a method for controlling differentiation of pluripotent stem cells, which method does not need a step of isolating specific cells from a cell population obtained by induced differentiation of pluripotent stem cells and is characterized by controlling the differentiation direction in the differentiation process of pluripotent stem cells into ocular cell primordium, thereby achieving the control of the cell composition in the iPS cell-derived cell population.

The present invention also relates to a simple method for producing, for example, a corneal epithelial cell population that can be used for the fabrication of corneal epithelial cell sheets for transplantation and a cell population containing specific eye-related cells other than corneal epithelial cells, by controlling the cell composition, and to use of a cell population obtained by the method.

The present invention also relates to an agent for controlling differentiation of pluripotent stem cells, which agent is capable of controlling the differentiation direction in the differentiation process of pluripotent stem cells into ocular cell primordium.

Solution to Problem

In order to solve the above-described problems, the present inventors conducted extensive research on the conditions for differentiation of iPS cells. As a result, the present inventors found that the proportion of differentiated cells in the iPS cell-derived cell population can be controlled by changing the type of the laminin used for induced differentiation. The key to selective differentiation is to appropriately select the growth factor and extracellular matrix added to culture medium as previously reported, but the present inventors first found that the direction of cell differentiation can be controlled as desired by changing the laminin isoforms used without changing the differentiation method.

That is, the present invention relates to the following [1] to [10].

[1] A method for controlling differentiation of pluripotent stem cells, the method comprising
selecting a laminin or a fragment thereof based on binding affinity for the pluripotent stem cells, and
inducing differentiation of the pluripotent stem cells in the presence of the laminin or a fragment thereof.
[2] The method according to the above [1], wherein the differentiation is induced in the presence of laminin 332 or a laminin 332E8 fragment and directed toward corneal epithelial cells.
[3] The method according to the above [1], wherein the differentiation is induced in the presence of laminin 111 or a laminin 111E8 fragment and directed toward neural cells.
[4] The method according to the above [1], wherein the differentiation is induced in the presence of laminin 211 or a laminin 211E8 fragment and directed toward neural crest cells.

[5] The method according to the above [1], wherein the differentiation is induced in the presence of laminin 411 or a laminin 411E8 fragment and directed toward retinal cells.
[6] The method according to the above [1], wherein the differentiation is induced in the presence of laminin 411 or a laminin 411E8 fragment and directed toward neural crest cells.
[7] A method for producing an eye-related cell population, comprising culturing differentiated cells derived from pluripotent stem cells by the method according to any one of the above [1] to [6].
[8] The method according to the above [7], wherein the cell population to be produced is a corneal epithelial cell population.
[9] A method for fabricating a corneal epithelial cell sheet for transplantation using a corneal epithelial cell population produced by the method according to the above [8].
[10] An agent for controlling differentiation of pluripotent stem cells, comprising a laminin selected from the group consisting of laminin 111, laminin 211, laminin 332, laminin 411 and laminin 511, or an E8 fragment thereof.

The present invention also includes the aspects described in the following [11] and [12].
[11] Use of a laminin selected from the group consisting of laminin 111, laminin 211, laminin 332, laminin 411 and laminin 511, or an E8 fragment thereof for controlling differentiation of pluripotent stem cells.
[12] A laminin selected from the group consisting of laminin 111, laminin 211, laminin 332, laminin 411 and laminin 511, or an E8 fragment thereof for use in controlling differentiation of pluripotent stem cells.

Advantageous Effects of Invention

According to the present invention, there is no need for a step of isolating desired cells from a cell population obtained by induced differentiation of pluripotent stem cells, and a simple procedure enables selective and large-scale production of, for example, a corneal epithelial cell population that can be used for the fabrication of corneal epithelial cell sheets for transplantation, from an eye-related cell population.

DESCRIPTION OF EMBODIMENTS

Figures 1, 2:
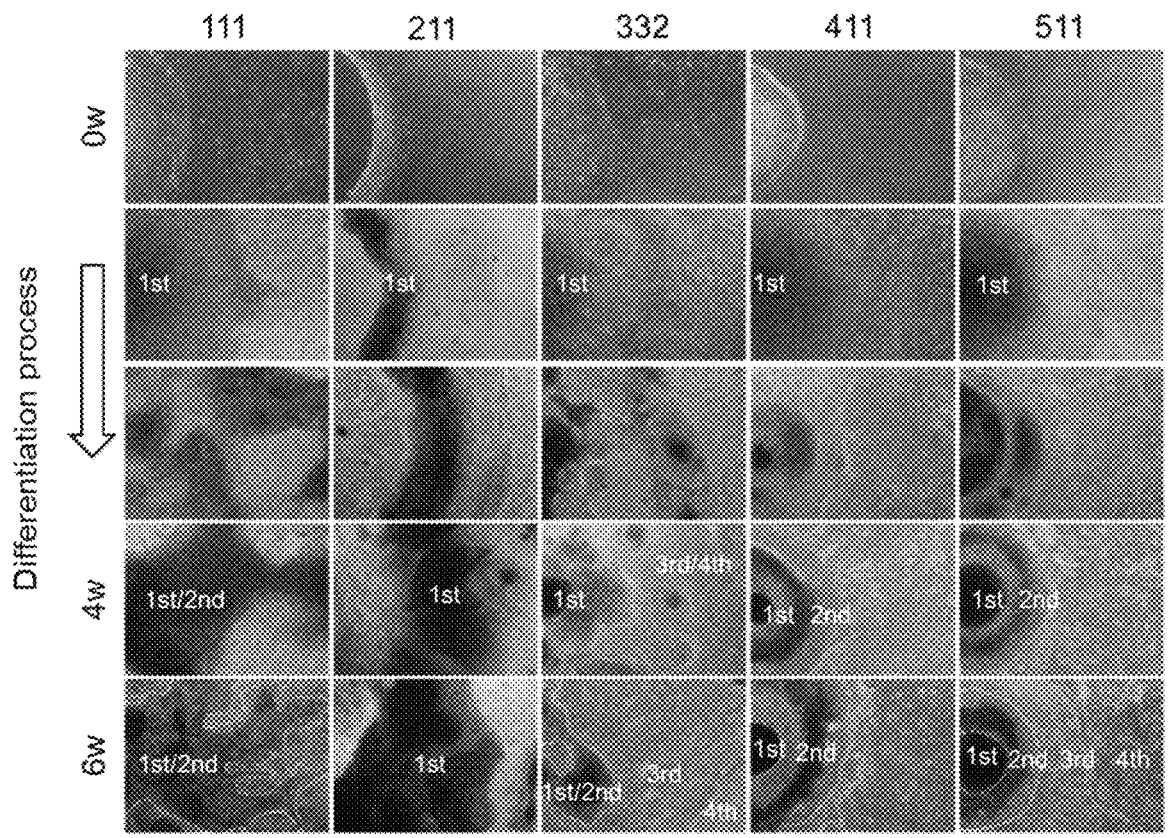
FIG. 1 shows a schematic representation of a method for inducing iPS cells to differentiate into eye-related cells.
FIG. 2 shows a representation of time-dependent morphological change of iPS cell-derived differentiated cells.

In Non Patent Literature 1, the present inventors obtained a cell population mimicking whole eye development from iPS cells using a laminin 511E8 fragment and collected only corneal epithelial (progenitor) cells from the obtained cell population by FACS-based purification to prepare a high-purity cell population. Here, the cell population mimicking whole eye development means a cell population including various types of eye cells in the developmental stage, for example, corneal epithelial cells, retinal cells, lens epithelial cells, neural crest cells, etc. Therefore, such a cell population has a potential to contribute to the development of regenerative medicine for separate ocular regions corresponding to different types of cells. However, under the current circumstances where some iPS cell lines have low differentiation efficiency, it is not easy even for the above method to prepare a cell population containing the desired cells in high purity from a cell population constituting the whole eye. In particular, there is a need for improved techniques that enable more quick and stable production of a corneal epithelial cell population. The present inventors examined the possibilities for such improvement focusing on laminin isoforms as an influencing factor in the development of ocular cells from pluripotent stem cells. As a result, the present inventors found that the cell composition of the produced cell population greatly varies depending on the type of the laminin isoform, that is, the type of the cell primordium and the differentiated cells obtained by differentiation of pluripotent stem cells greatly varies depending on the type of the laminin isoform. A plausible mechanism of such selective differentiation is as follows. The difference in binding affinity of the laminin isoform for pluripotent stem cells causes changes in cell migration, cytoskeleton, adhesion, or suspending conditions, thus generating isoform-dependent polarity in pluripotent stem cell colonies and changes in the differentiation-related transcription factors and signaling pathways. As a result, autonomous differentiation of various types of cells is influenced, and further, cell primordium and differentiated cells expressing an integrin subunit having a high specific binding affinity for the laminin isoform used are selectively proliferated, ultimately leading to the difference in the cell composition of the produced cell population. Therefore, for example, even when the same growth factor is used in the medium, selective differentiation into various types of cells can be achieved by using an appropriate isoform selected based on the binding affinity for pluripotent stem cells. In addition, after primordium formation, the use of a particular laminin isoform selected as appropriate for the type of the integrin expressed in the primordium can further promote selective proliferation into the desired cells. However, the above speculation shall not be construed as limiting the present invention.

The present invention provides a method for controlling differentiation of pluripotent stem cells, which method is characterized by inducing differentiation of pluripotent stem cells in the presence of a laminin or a fragment thereof selected as appropriate for the type of the desired differentiated cells. More specifically, a particular laminin or a fragment thereof corresponding to the type of the desired differentiated cells is selected based on the binding affinity for pluripotent stem cells, and differentiation of pluripotent stem cells is induced in the presence of the laminin or a fragment thereof, thereby achieving the control of the direction of differentiation. For example, according to the method, a cell population rich in corneal epithelial cells and a cell population rich in neural crest cell can be separately produced by using different types of laminins or fragments thereof in the presence of the same growth factor that induces differentiation into eye-related cells. In other words, various differentiated cells can be separately produced from the same pluripotent stem cells by using different types of laminins or fragments thereof. Therefore, the method of the present invention for controlling differentiation of pluripotent stem cells is also a method for inducing selective differentiation of pluripotent stem cells into desired differentiated cells, a method for selecting desired differentiated cells, or a method for producing a cell population rich in desired cells. Here, the cell population rich in specific cells means a cell population containing a higher proportion of specific cells as compared with a cell population obtained by induced differentiation under the same conditions except for the absence of the corresponding laminin or a fragment thereof, and the proportion is not particularly limited.

The pluripotent stem cells in the present invention are stem cells which have pluripotency, i.e., the ability to differentiate into any type of cells present in a living body, and proliferative capacity. Specific examples of the stem cells include embryonic stem cells (ES cells), embryonic stem cells from a cloned embryo obtained by nuclear transfer (ntES cells), spermatogenic stem cells (GS cells), embryonic germ cells (EG cells), induced pluripotent stem cells (iPS cells), and pluripotent cells from cultured fibroblasts or myeloid stem cells (Muse cells). Preferred are ES cells, ntES cells and iPS cells, and more preferred are iPS cells. The pluripotent stem cells are preferably pluripotent stem cells of mammals. The mammal is not particularly limited, and examples include humans, mice, rats, cattle and pigs. Particularly preferred are humans. With the use of human pluripotent stem cells, a particular cell population that is safe and compatible for use in human regenerative medicine can be obtained.

Laminin is a heterotrimeric molecule consisting of three subunits termed α, β and γ chains. Five kinds of α chains (α1 to α5), three kinds of β chains (β1 to β3) and three kinds of γ chains (γ1 to γ3) are known, and various combinations of these chains result in at least 12 kinds of laminin isoforms (see Table 1). The laminin used in the present invention may be any of these isoforms, and any appropriate laminin composed of a combination of an α chain selected from α1 to α5, a β chain selected from β1 to β3, a γ chains selected from γ1 to γ3 may be selected depending on the type of the desired differentiated cells. As used herein, a laminin isoform composed of an α1 chain, a β1 chain and a γ1 chain is written in abbreviation as "laminin 111". The same may apply to other isoforms.

TABLE 1

| α chain | Trimer composition | |
| --- | --- | --- |
| α1 | α1β1γ1 | (laminin-1) |
|    | α1β2γ1 | (laminin-3) |
| α2 | α2β1γ1 | (laminin-2) |
|    | α2β2γ1 | (laminin-4) |
|    | α2β1γ3 | (laminin-12) |
| α3 | α3β3γ2 | (laminin-5) |
|    | α3β1γ1 | (laminin-6) |
|    | α3β2γ1 | (laminin-7) |
| α4 | α4β1γ1 | (laminin-8) |
|    | α4β2γ1 | (laminin-9) |
| α5 | α5β1γ1 | (laminin-10) |
|    | α5β2γ1 | (laminin-11) |

The origin of the laminin is not particularly limited, and laminins of various organisms can be used. Preferred are laminins of mammals. Examples of the mammal include but are not limited to humans, mice, rats, cattle and pigs. The species of origin of the laminin is preferably the same as that of the pluripotent stem cells to be used. For example, in the case where human stem cells are cultured for preparation of materials for human regenerative medicine, human laminins are preferably used.

The laminin used in the present invention may be a full-length laminin or a fragment thereof. That is, the laminin maybe a full-length laminin consisting of a full-length α chain, a full-length β chain and a full-length γ chain, or a laminin fragment consisting of α, β and γ chains of which one or more are fragments shorter than the corresponding full-length chains. The laminin fragment is required to be in the form of a heterotrimer. The laminin fragment preferably has integrin binding activity.

The laminin fragment can be, for example, an E8 fragment of the laminin described above. The laminin E8 fragment (hereinafter referred to as "laminin E8" or "E8"), which is a heterotrimeric fragment obtained by elastase digestion of mouse laminin 111, was identified as having strong cell-adhesive activity (Edgar D et al., J. Cell Biol., 105: 589-598, 1987). Elastase digestion of laminins other than mouse laminin 111 could presumably produce fragments corresponding to the mouse laminin 111E8, but there has been no report on isolation or identification of such E8 fragments. Therefore, the laminin E8 used in the present invention does not have to be an elastase-digestion product of laminins and may be any laminin fragment equivalent in cell-adhesive activity and structure to the mouse laminin 111E8.

Laminin E8 is a trimeric fragment composed of a C-terminal fragment of the α chain lacking globular domains 4 and 5 (α chain E8), a C-terminal fragment of the β chain (β chain E8), and a C-terminal fragment of the γ chain (γ chain E8). The molecular weight of the trimer is not particularly limited but is usually about 150 to 170 kDa. The glutamic acid residue at the 3rd position from the C-terminus of the γ chain E8 is essential for the integrin binding activity of laminin E8 (Hiroyuki Ido et al., The Journal of Biological Chemistry, 282, 11144-11154, 2007).

The heterotrimer formation and the integrin binding activity of the laminin and the laminin fragment can be confirmed by known methods. The heterotrimer formation can be confirmed from, for example, the number of bands detected by SDS-PAGE. The integrin binding activity can be confirmed by, for example, ELISA or the like.

The laminin may be a native laminin or a modified laminin that has modification of one or more amino acid residues but retains biological activities of the native laminin. The same shall apply to the laminin fragment. The method for producing the laminin is not particularly limited. For example, the laminin can be obtained by purification from cells highly expressing the laminin. Alternatively, the laminin can be produced as a recombinant protein. The method for producing the laminin fragment is also not particularly limited. For example, the laminin fragment can be obtained by digestion of a full-length laminin with a protease such as elastase, followed by isolation and purification of the fragment of interest. Alternatively, the laminin fragment can be produced as a recombinant protein. In terms of production quantity, quality uniformity, production cost, etc., it is preferred that the laminin and the laminin fragment are produced as recombinant proteins.

The recombinant laminin and the recombinant laminin fragment can be produced by appropriate known recombinant techniques, for example, by preparing DNAs encoding full-length laminin α, β and γ chains or preparing DNAs encoding E8 fragments of these chains (in the case of the production of recombinant laminin E8), inserting the DNAs into separate expression vectors, co-introducing the three resulting expression vectors into appropriate host cells, and purifying the expressed trimeric protein by a known method. The production method of the recombinant laminin (full-length) may be, for example, the method of Ido et al. (Hiroyuki Ido et al., The Journal of Biological Chemistry, 279, 10946-10954, 2004), but is not limited thereto. The production method of the recombinant laminin E8 may be, for example, the method of Ido et al. (Hiroyuki Ido et al., The Journal of Biological Chemistry, 282, 11144-11154, 2007), but is not limited thereto.

Information regarding the nucleotide sequences of the genes encoding laminin α, β and γ chains of major mammals and the amino acid sequences of these chains can be obtained from known databases (e.g., GenBank, etc.). The accession numbers of the constituent chains of human laminins are shown in Table 2. Information regarding the nucleotide and amino acid sequences of the constituent chains of laminins of other organisms can also be obtained from known databases (e.g., GenBank etc.).

TABLE 2

|  | Amino acid sequence | Nucleotide sequence |
|---|---|---|
| Human laminin α1 chain | NP_005550 | NM_005559 |
| Human laminin α2 chain | NP_000417 | NM_000426 |
| Human laminin α3 chain | NP_000218 | NM_000227 |
| Human laminin α4 chain | NP_002281 | NM_002290 |
| Human laminin α5 chain | NP_005551 | NM_005560 |
| Human laminin β1 chain | NP_002282 | NM_002291 |
| Human laminin β2 chain | NP_002283 | NM_002292 |
| Human laminin β3 chain | NP_000219 | NM_000228 |
| Human laminin γ1 chain | NP_002284 | NM_002293 |
| Human laminin γ2 chain | NP_005553 | NM_005562 |
| Human laminin γ3 chain | NP_006050 | NM_006059 |

The laminin used in the present invention may be one kind or a combination of two or more kinds selected from the group consisting of the above-described laminins and is selected as appropriate for the type of the desired differentiated cells based on the binding affinity for the pluripotent stem cells. The same applies to the laminin fragment. That is, the laminin and the laminin fragment used in the present invention are selected as appropriate for the type of the desired differentiated cells, and for this selection, the binding affinity for pluripotent stem cells is used. The binding affinity for cells herein can be assessed by time-course observation of the survival rate and motility of the cells. In addition, the measurement of integrin binding activity by ELISA or the like is also useful for the assessment of the binding affinity for cells. Alternatively, the binding affinity for cells can be assessed with reference to the dissociation constants of recombinant integrins for laminin isoforms listed in Table 3 of reference 1 (Matrix Biol. 2006 Apr;25 (3):189-97. Epub 2006 Jan. 18.). For example, the table given below shows the binding affinities for pluripotent stem cells assessed based on the dissociation constants of laminin-binding integrins expressed in iPS cells shown in reference 1. The binding affinities of other laminin isoforms can also be assessed by comparison with the data in the table given below.

TABLE 3

|  | Laminin | | | | |
|---|---|---|---|---|---|
| Kd (nM) | 111 | 211/221 | 332 | 411 | 511/521 |
| α3β1 | ND | ND (+) | 14 ± 3 | ND | 3.4 ± 0.8 |
| α6β1 | 9.5 ± 3.3 | ND (+) | 7.5 ± 2.7 | ND (+) | 0.73 ± 0.22 |
| α6β4 | ND | ND | 12 ± 3 | ND | 25 ± 1 |
| α7χ1β1 | ND (+) | 0.64 ± 0.35 | ND | ND (+) | 1.2 ± 0.5 |
| α7χ2β1 | 0.97 ± 0.26 | 2.6 ± 0.7 | ND | ND | ND (+) |

TABLE 3-continued

| | Laminin | | | | |
|---|---|---|---|---|---|
| Kd (nM) | 111 | 211/221 | 332 | 411 | 511/521 |
| Binding affinity for pluripotent stem cells | Moderate | Weak | Moderate | Weak (slightly strong at 2-fold coating concentration) | Strong |

* ND: Not Determined, ND (+): Measurement Limit Level

Based on the binding affinity assessed as described above, isoforms with strong binding affinity for pluripotent stem cells are selected to induce differentiation into central neural cells, retinal cells, etc.; isoforms with moderate binding affinity for pluripotent stem cells are selected to induce differentiation into epithelial cells such as corneal epithelial cells, epidermal cells and lens epithelial cells; and isoforms with weak binding affinity for pluripotent stem cells are selected to induce differentiation into neural cells, neural crest cells, etc. That is, the selection of the type of the laminin or the laminin fragment to be used depends on the desired differentiated cells. The desired cells or cell primordium can be formed by culturing pluripotent stem cells in the presence of the thus-selected laminin or laminin fragment.

The method for differentiation of pluripotent stem cells can be selected as appropriate from known methods as long as differentiation can be achieved in the presence of the laminin or a fragment thereof. For example, the method developed by the present inventors to induce pluripotent stem cells to differentiate into eye-related cells (Non Patent Literature 1) can preferably be used. More specifically, the culture surface of a culture vessel such as a culture dish is coated with the laminin or the laminin fragment, and human iPS cells are seeded thereon and cultured for several days to form colonies, followed by culture in a medium containing KnockOut Serum Replacement and subsequent culture in a medium containing human keratinocyte growth factor (KGF) and human fibroblast growth factor-2 (FGF-2). The culture for colony formation may be referred to as "colony forming culture", and the culture thereafter may be referred to as "differentiation culture" or "induced differentiation". In another example of the differentiation method, a carrier, such as beads, is coated with the laminin or the laminin fragment and added to a cell suspension, followed by cell culture. In yet another example, the laminin or the laminin fragment is directly added to culture medium, followed by cell culture. In the present invention, the amount and the type of the laminin or a fragment thereof may be changed or not be changed at medium replacement.

The concentration of the laminin or the laminin fragment used is selected as appropriate for the type of the laminin or the laminin fragment, that is, as appropriate for the binding affinity for pluripotent stem cells such that the purpose can be achieved. For example, in the case where the laminin or the laminin fragment is used for coating, the concentration of the laminin or the laminin fragment can be selected from the range of about 0.1 to 10 µg/cm². In particular, in the case where laminin E8 is used for coating, the concentration of laminin E8 may be about 0.25 to 2.0 µg/cm², about 0.5 to 1.5 µg/cm², and about 0.5 to 1.0 µg/cm². Also, in the case where the laminin or the laminin fragment is added to culture medium, the amount of the laminin or the laminin fragment can be selected as appropriate for the culture area of a culture vessel such that the amount corresponds to the coating amount described above. For example, laminin isoforms have strong binding affinity for pluripotent stem cells may be used at low concentration to adjust the binding affinity for the desired control of induced differentiation. The method for immobilizing the laminin or the laminin fragment on a culture vessel (coating method) is not particularly limited, and for example, the laminin or the laminin fragment can be immobilized by contact with the solid phase in an appropriate buffer solution.

The medium used in the present invention is not particularly limited, and a known medium prepared by mixing the ingredients required for cell culture can be used. For example, an appropriate commercial medium can be selected and used. Such a medium may contain an ingredient(s) other than essential components of the medium.

Specifically, for example, a growth factor appropriate for the type of the desired differentiated cells may be contained. The growth factor can be selected as appropriate according to the known art, and examples include KGF, FGF-2 and BMP4.

The number of cells at the start of culture is not particularly limited, and is for example, preferably 10 to $1\times10^8$ cells/mL, more preferably $1\times10^2$ to $5\times10^7$ cells/mL, still more preferably $1\times10^3$ to $2\times10^7$ cells/mL. In the case of adherent culture, the number of cells at the start of culture is, for example, preferably 10 to 2,500 cells/cm², more preferably 100 to 1,000 cells/cm², and still more preferably 300 to 700 cells/cm². The culture conditions are not particularly limited, and the conditions for the usual cell culture can be used. For example, cells may be cultured at 37° C. and 5% $CO_2$ etc. During the culture, fresh medium may be added for dilution of the cell culture medium at appropriate time intervals, or medium or cell culture vessel may be replaced at appropriate time intervals.

There is no particular limitation on the cell culture vessel that can be used in the present invention, and for example, a dish (plate), a flask, a bag, a large-sized culture tank, a bioreactor, etc. can be used. The bag may be, for example, a $CO_2$-permeable bag for cell culture. For large-scale industrial production of cell populations, a large-sized culture tank can be used. Cells may be cultured in an open system or a closed system, but preferred is a closed system for securing the safety of cell populations to be prepared.

There is no particular limitation on the duration for which pluripotent stem cells are cultured in the presence of the laminin or the laminin fragment. The duration is selected as appropriate for the type and the amount of the laminin or the laminin fragment such that the purpose can be achieved. The duration for which the laminin or the laminin fragment is present during culture may be the whole or any part of the culture period. Preferably, the cells are cultured in the presence of the laminin or the laminin fragment at least at the early phase, preferably at the beginning of the whole culture period.

In the present invention, after the desired cell primordium is formed by culturing pluripotent stem cells in the presence of the laminin or the laminin fragment, selective proliferation can be induced with the use of an isoform selected as appropriate for the type of the integrin expressed in the cell primordium. Such induced differentiation is also included in the present invention. Specifically, for example, differentiation into neural crest cells can be induced by culturing the cell primordium in the presence of laminin 211 or a fragment thereof; differentiation into epithelial cells can be induced by culturing the cell primordium in the presence of laminin 332 or a fragment thereof; and differentiation into retinal cells or neural crest cells can be induced by culturing the cell primordium in the presence of laminin 411 or a fragment thereof.

In the present invention, culture is performed in the presence of a substance other than the laminin or the laminin fragment as desired. Examples of such an additional substance include vitronectin, fibronectin, collagen, Matrigel, gelatin and poly-L-lysine.

In addition, to promote differentiation, other substances may be added as appropriate for the type of the desired differentiated cells. For example, a Wnt signaling pathway activator may be added for promotion of differentiation into neural crest cells.

As described above, differentiation of pluripotent stem cells is induced in the presence of the laminin or the laminin fragment appropriate for the type of the desired cells, to selectively produce the desired cell population.

The differentiated cells are not particularly limited and are exemplified by any somatic cells into which pluripotent stem cells can be differentiated. Specific examples include ectoderm-derived cells such as corneal cells, dopamine-producing neurons, motor neurons, peripheral neurons, pigment epithelial cells, skin cells and inner ear cells. Also included are entoderm-derived cells such as hepatocytes, pancreatic progenitor cells, insulin-producing cells, cholangiocytes, alveolar epithelial cells and intestinal epithelial cells. Also included are mesoderm-derived cells such as cardiomyocytes, skeletal muscle cells, vascular endothelial cells, hepatocytes, osteocytes, chondrocytes, renal progenitor cells and renal epithelial cells. The somatic cells include not only terminally differentiated mature cells but also cells which are in the middle of differentiation and have yet to terminally differentiate.

The proportion of the desired cells in the obtained cell population may vary with the type of the laminin or the laminin fragment used and/or the culture conditions used, and therefore, cannot be definitely specified.

There is no particular limitation on the method for collecting the desired cells from the obtained cell population. The method for collecting cells not adherent to the laminin or the laminin fragment (non-adherent cells) is, for example, as follows. In the case where a culture vessel coated with the laminin or the laminin fragment is used, the medium is collected from the culture vessel, the coated surface is washed a few times with PBS or the like, and the collected medium and wash solution are subjected to centrifugation or the like to collect the cells contained therein. In the case where a carrier coated with the laminin or the laminin fragment has been added to a cell suspension, the cell suspension after collection of the carrier is subjected to centrifugation or the like to collect the cells remaining therein.

The method for collecting cells adherent to the laminin or the laminin fragment (adherent cells) is not particularly limited, and any appropriate known method for detaching adherent cells may be selected. In the case where a culture vessel coated with the laminin or the laminin fragment is used, for example, non-adherent cells are removed, a known cell detachment solution, such as an EDTA solution or a trypsin solution, is added onto the surface coated with the laminin or the laminin fragment, and adherent cells are detached by pipetting or the like and then collected. In the case where a carrier coated with the laminin or the laminin fragment is used, for example, the carrier is added to a cell detachment solution, and the adherent cells are detached by pipetting or the like and then collected.

As described above, the method of the present invention for controlling differentiation of pluripotent stem cells enables the control of differentiation of pluripotent stem cells into the desired cells with the use of laminins, and is greatly advantageous in that a cell population rich in the desired cells can be produced. In addition, since the desired cells can be directly obtained from pluripotent stem cells, the method of the present invention requires a smaller number of steps and is more productive as compared with the method of Non Patent Literature 1. Laminins are known to prevent cell apoptosis and maintain cell survival as well as activate intracellular signaling pathways for cell growth promotion (Gu J et al. The Journal of Biological Chemistry 277:19922-19928, 2002). The present invention, which uses the laminin or the laminin fragment during cell differentiation, is greatly advantageous in that the resulting cell population has a high viability.

Hereinafter, exemplary methods for inducing selective differentiation into eye-related cells will be described. Specifically, the methods use a laminin selected from the group consisting of laminin 111, laminin 211, laminin 332, laminin 411 and laminin 511, or an E8 fragment thereof. The methods use the same culture conditions except for using different types of laminins or laminin fragments. The culture conditions may be as described above.

Laminin 111 is an isoform composed of an α1 chain, a β1 chain, and a γ1 chain and may be referred to as "laminin 1" or "laminin α1β1γ1". Laminin 111 is known to be expressed in the basement membrane of embryonic tissues. Laminin 111 or an E8 fragment thereof is suitable for inducing differentiation into neural cells, neuroretina, and lens epithelial cells.

Laminin 211 is an isoform composed of an α2 chain, a β1 chain, and a γ1 chain and may be referred to as "laminin 2" or "laminin α2β1γ1". Laminin 211 is known to be expressed specifically in the basement membrane of muscle tissues and nervous tissues. Laminin 211 or an E8 fragment thereof is suitable for inducing differentiation into neural cells and neural crest cells. Laminin 211 or an E8 fragment thereof has a very weak binding affinity for pluripotent stem cells, but pluripotent stem cells can adhere and survive on laminin 211 or an E8 fragment thereof. For this reason, pluripotent stem cells can be subjected to adherent culture on laminin 211 or an E8 fragment thereof in the conditions almost similar to those of suspension culture, which is used for inducing differentiation into neural cells. This helps to activate Wnt signaling, resulting in differentiation into neural cells and neural crest cells, which attach and migrate. Addition of a Wnt signaling pathway activator to the culture further promotes the differentiation into neural crest cells. In iPS cells cultured on laminin 211, which promotes the differentiation into neural cells and neural crest cells, phosphorylation of vinculin at Y822 is enhanced, and cell-cell adhesion is predominant.

Laminin 332 is an isoform composed of an α3 chain, a β3 chain, and a γ2 chain and may be referred to as "laminin 5" or "laminin α3β3γ2". Laminin 332 is known to be expressed specifically in the basement membrane of stratified epithelial tissues such as the skin. Pluripotent stem cells adhere well on laminin 332, and laminin 332 can be used for colony forming culture. Due to the moderate binding affinity of laminin 332, collective cell migration is active on laminin 332 during the colony forming process, resulting in a relatively low cell density in the colonies. This makes it unlikely to activate the pathway which promotes neuroectodermal differentiation, thus facilitating differentiation into surface ectoderm. In addition, the binding affinity of laminin 332 is low for neural cells, neuroretinal cells, etc. and is high for epithelial cells. Therefore, laminin 332 is suitable for inducing differentiation into epithelial cells, in particular, corneal epithelial cells.

Laminin 411 is an isoform composed of an α4 chain, a β1 chain, and a γ1 chain and may be referred to as "laminin 8" or "laminin α4β1γ1". Laminin 411 is known to be expressed specifically in the basement membrane of vascular endothelium etc. Laminin 411 or an E8 fragment thereof is suitable for inducing differentiation into neuroretinal cells, neural crest cells, etc. The use of laminin 411 or an E8 fragment thereof at high concentration, due to the strong binding affinity for pluripotent stem cells, hinders collective cell migration, resulting in a relatively high cell density in the colonies, as with the case of laminin 511 described later. This helps to activate the pathway which promotes neuroectodermal differentiation at the colony center, thus facilitating differentiation into neuroectodermal lineages. In addition, the binding affinity of laminin 411 or an E8 fragment thereof for neural crest cells and retinal cells is higher than that for epithelial cells, and therefore subsequent retinal growth is promoted.

Laminin 511 is an isoform composed of an α5 chain, a β1 chain, and a γ1 chain and may be referred to as "laminin 10" or "laminin α5β1γ1". Laminin 511 is known to be expressed specifically in the basement membrane of the kidney, the lung, the pancreas, blood vessels, etc. Laminin 511 or an E8 fragment thereof is known to be useful for balanced induction of differentiation into neurons, the retina, epithelial cells, etc. However, the use of laminin 511 or an E8 fragment thereof at higher concentration, due to the strong binding affinity for pluripotent stem cells, hinders collective cell migration, resulting in a relatively high cell density in the colonies, in particular, at the colony center. This helps to activate the pathway which promotes neuroectodermal differentiation at the colony center, thus facilitating differentiation into neuroectodermal lineages. In contrast, laminin 511 or an E8 fragment thereof at lower concentration promotes collective cell migration and can induce differentiation into epithelial cells. In addition, the use of laminin 511 or an E8 fragment thereof at high concentration induces MLC phosphorylation and is likely to result in constriction at the colony periphery.

As described above, with the use of a laminin selected from the group consisting of laminin 111, laminin 211, laminin 332, laminin 411, and laminin 511, or an E8 fragment thereof, eye-related cell populations each of which is rich in a different type of cells can be produced.

That is, the present invention also provides a method for producing at least one eye-related cell population selected from the group consisting of:
cell population 1: a cell population rich in retinal cells;
cell population 2: a cell population rich in neural crest cells;
cell population 3: a cell population rich in neural cells; and
cell population 4: a cell population rich in corneal epithelial cells,
using the method of the present invention for controlling differentiation of pluripotent stem cells.

The method of the present invention for producing a cell population is not particularly limited as long as the method of the present invention for controlling differentiation of pluripotent stem cells is employed. For example, a cell population rich in corneal epithelial cells can be produced by culturing pluripotent stem cells in the presence of laminin 332 or laminin 332E8. For the details of the culture procedure, culture conditions, etc., see the section for the method of the present invention for controlling differentiation of pluripotent stem cells.

The use of laminin 332 or laminin 332E8, due to the moderate binding affinity for pluripotent stem cells, facilitates collective cell migration during the colony forming process, resulting in a relative low cell density in the colonies. This makes it unlikely to activate the Hippo pathway, thus facilitating differentiation into surface ectoderm, which is the corneal epithelial or epidermal primordium. The use of the laminin or the laminin fragment with strong binding affinity for pluripotent stem cells advantageously promotes epithelial cell differentiation and halves the time required for such differentiation as compared with the use of laminin 511E8 described in Non Patent Literature 1. More advantageously, such promoted differentiation results in a reduced proportion of undifferentiated cells and tumorigenic cells in the obtained cells. Therefore, the production method of the present invention has a great advantage of producing corneal epithelial cells in a highly productive manner.

The cell population produced by the production method of the present invention, for example, cell population (4) is a high-purity corneal epithelial cell population that can be directly cultured for fabrication into a corneal epithelial cell sheet for transplantation. The "corneal epithelial cell population for the fabrication of corneal epithelial cell sheets for transplantation" has to be a cell population composed of $1 \times 10^5$ cells or more, which cell number is needed for the fabrication of a corneal epithelial cell sheet for at least one eye. However, in consideration of the industrial application of the present invention, the "corneal epithelial cell population for the fabrication of corneal epithelial cell sheets for transplantation" desirably contains the number of cells needed for the fabrication of corneal epithelial cell sheets for more than one eye. Therefore, the number of cells in the "corneal epithelial cell population for the fabrication of corneal epithelial cell sheets for transplantation" is preferably $2 \times 10^5$ cells or more, $4 \times 10^5$ cells or more, $6 \times 10^5$ cells or more, $8 \times 10^5$ cells or more, or $1 \times 10^6$ cells or more. In addition, the "corneal epithelial cell population for the fabrication of corneal epithelial cell sheets for transplantation" preferably has a contaminant cell content of less than 50%, less than 45%, less than 40%, less than 35%, or less than 30%.

The corneal epithelial cell sheet for transplantation can be fabricated by seeding the cell population produced by the production method of the present invention at $1.5 \times 10^5$ to $6.0 \times 10^3$ cells/well on a 6-well plate or at $0.5 \times 10^5$ to $1.0 \times 10^5$ cells/well on a 12-well plate, followed by culturing to confluency for 5 to 12 days.

The corneal epithelial cell population produced by the production method of the present invention can be directly used as a material of corneal epithelial cell sheets for transplantation. Therefore, the present invention includes a method for fabricating a corneal epithelial cell sheet for transplantation, which method comprises the step of culturing a corneal epithelial cell population produced by the production method of the present invention. There is no particular limitation on the method for fabricating a corneal epithelial cell sheet for transplantation from a corneal epithelial cell population produced by the production method of the present invention. For example, the cell population produced by the production method of the present invention is seeded at $1.5 \times 10^5$ to $6.0 \times 10^3$ cells/well on a 6-well plate or at $0.5 \times 10^5$ to $1.0 \times 10^3$ cells/well on a 12-well plate, and cultured to confluency for 5 to 12 days. Medium replacement is preferably performed once every two days. The plates may be typical cell culture plates. Alternatively, a temperature-responsive cell cultureware for cell sheet engineering ("UpCell (trade name)" manufactured by CellSeed) may be used.

In addition, the cell population produced by the method of the present invention, which is rich in specific cells, can greatly contribute to, for example, the drug efficacy evaluation of therapeutic agents for eye diseases, the analysis of pathogenic mechanisms of eye diseases, etc.

The present invention also provides an agent for controlling differentiation of pluripotent stem cells, comprising a laminin selected from the group consisting of laminin 111, laminin 211, laminin 332, laminin 411, and laminin 511, or a fragment thereof. The agent of the present invention for controlling differentiation of pluripotent stem cells, which uses the laminin or the laminin fragment, is capable of inducing selective differentiation of pluripotent stem cells into desired cells. For details, see the section for the method of the present invention for controlling differentiation of pluripotent stem cells.

EXAMPLES

Hereinafter, the present invention will be described in detail by the following examples which are for illustrative purposes only and are not intended to be limiting. Henceforth, "room temperature" refers to 25° C.

Example 1

Induced Differentiation into Eye-related Cells

For induced differentiation of iPS cells into eye-related cells, the protocol for self-formed ectodermal autonomous multi-zone (SEAM) formation (Hayashi et al. Nature 2016 Mar 17;531(7594):376-80.) was used. A schematic representation of the steps involved in the induced differentiation is shown in FIG. 1. The laminin isoforms used were a laminin 111E8 fragment (laminin 111E8), a laminin 211E8 fragment (laminin 211E8), a laminin 332E8 fragment (laminin 332E8), a laminin 411E8 fragment (laminin 411E8) and a laminin 511E8 fragment (laminin 511E8), all of which were prepared according to the known art.

The specific procedure of the induced differentiation was as follows. Human iPS cells (201B7) were seeded at a density of 300 to 700 cells/cm$^2$ on plates coated with E8 fragments of different laminin isoforms at a concentration of 0.5 to 1.0 μg/cm$^2$, cultured for 8 to 10 days in StemFit (registered trademark) medium (Ajinomoto), and cultured for 4 weeks in a differentiation medium (DM; GMEM (Life Technologies) supplemented with 10% knockout serum replacement (KSR, Life technologies), 1 mM sodium pyruvate (Life Technologies), 0.1 mM non-essential amino acids (Life Technologies), 2 mM L-glutamine (Life Technologies), 1% penicillin-streptomycin solution (Life Technologies) and 55 μM 2-mercaptoethanol (Life Technologies)). After that, culture was continued for 4 weeks in corneal differentiation medium (CDM; a 1:1 (v/v) mixed medium of DM and Cnt-20 or Cnt-PR medium (without EGF or FGF2, CeLLnTEC Advanced Cell Systems) supplemented with 20 ng/mL KGF (Wako), 10 μM Y-27632 (Wako) and 1% penicillin-streptomycin solution) and subsequently for additional 2 to 5 weeks in corneal epithelial cell maintenance medium (CEM; DMEM/F12 (2:1 (v/v)) (Life Technologies) supplemented with 2% B27 supplement (Life Technologies), 1% penicillin-streptomycin solution, 20 ng/mL KGF and 10 μM Y-27632) for induced differentiation. The sample obtained on laminin 511E8 is an example of induced differentiation as described in Non Patent Literature 1.

The phase contrast images of cell morphology in the differentiation process on each laminin isoform were acquired using Axio Observer.D1 (Carl Zeiss). The results are shown in FIG. 2. In the figure, "111" represents an example using laminin 111E8, "211" represents an example using laminin 211E8, "332" represents an example using laminin 332E8, "411" represents an example using laminin 411E8, and "511" represents an example using laminin 511E8. The same abbreviation will be used in the following Examples.

As is clear from FIG. 2, the SEAM formed on "511" as described in Non Patent Literature 1 was composed of four zones, i.e., the first zone (1st in the figure), the second zone (2nd in the figure), the third zone (3rd in the figure), and the fourth zone (4th in the figure), which constituted the central nerve, the retina, the corneal epithelium, and epithelial cells other than the cornea, respectively. The image of "111" after 6 weeks shows the induction of the first and second zones (1st/2nd), the image of "211" after 6 weeks shows the induction of the first zone (1st), and the image of "332" after 6 weeks shows the induction of the third and fourth zones (3rd/4th). The structure formed on "411" seemingly resembled but differed from that formed on "511" in that the former lacked the third and fourth zones (3rd/4th). These results demonstrate that, in the differentiation process of pluripotent stem cells into ocular cells containing various eye-related cells, selective differentiation into a particular zone can be achieved using a particular type of isoform.

Example 2

Marker Protein Expression in Differentiated Cells

Figure 3:
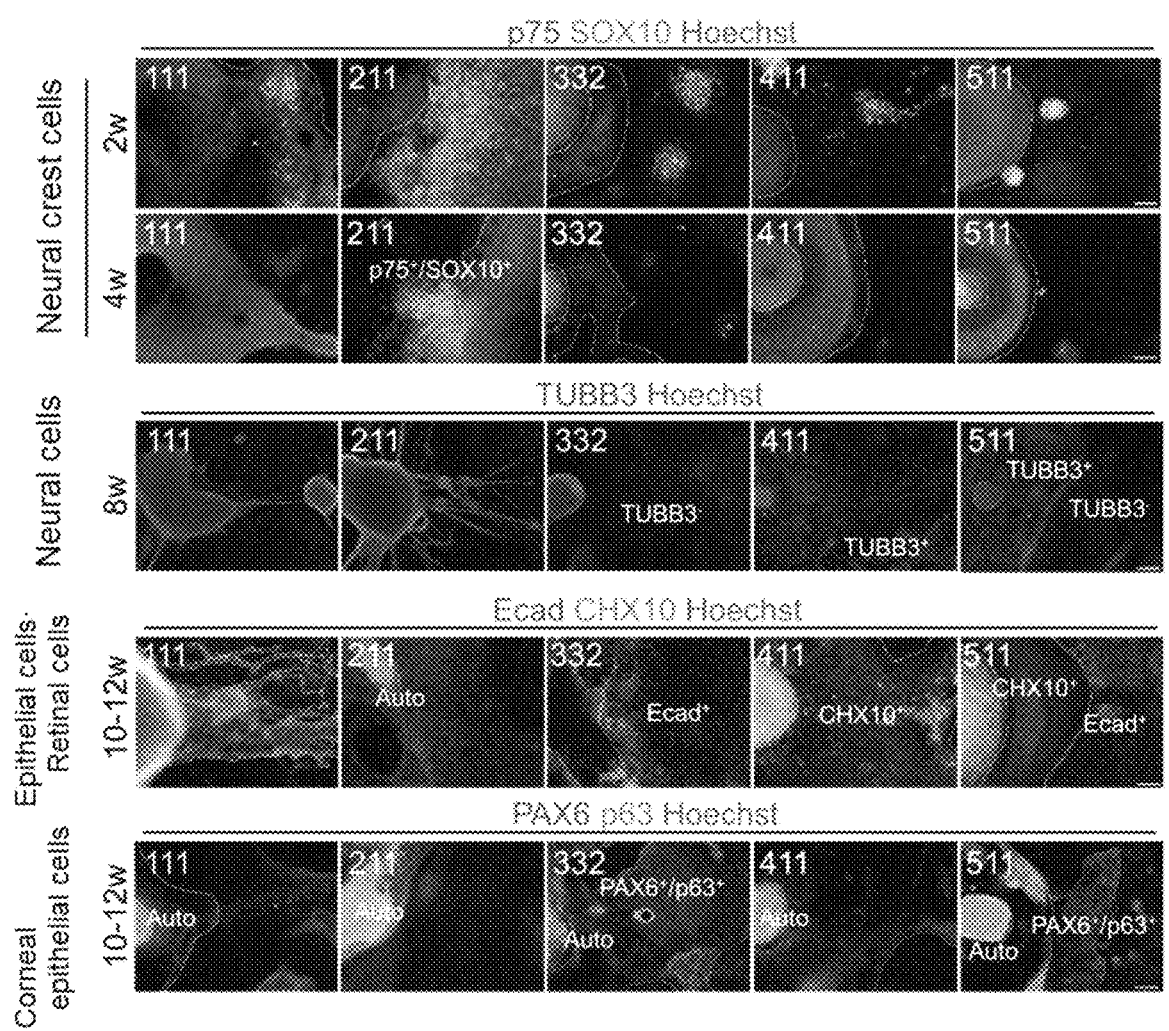
FIG. 3 shows a representation of marker proteins expressed in iPS cell-derived differentiated cells.

Cell differentiation was induced as described in Example 1. After an appropriate period of culture, the medium was removed, followed by washing with PBS and subsequent fixation with 4% paraformaldehyde/PBS or cold methanol. After 3 times of washing with TBS, the cells were blocked with TBS containing 5% normal donkey serum and 0.3% Triton-X 100 at room temperature for 1 hour and then reacted with the primary antibody at room temperature for 1 hour or at 4° C. overnight. After 3 times of washing with TBS, the cells were reacted with the secondary antibody at room temperature for 1 hour. As the primary antibodies for the detection of neural crest cells, an anti-p75 antibody (mouse monoclonal; ME20.4, ADVANCED TRGETING SYSTEMS) and an anti-SOX10 antibody (goat polyclonal; N-20, Santa Cruz Biotechnology) were used. As the primary antibody for the detection of neural cells, an anti-TUBB3 antibody (rabbit polyclonal; T2200, Sigma-Aldrich) was used. As the primary antibodies for the detection of epithelial cells and retinal cells, an anti-E-cadherin antibody (mouse monoclonal; 180215, R&D systems) and an anti-CHX10 antibody (goat polyclonal; N-18, Santa Cruz Biotechnology) were used, respectively. As the primary antibodies for the detection of corneal epithelial cells, an anti-PAX6 antibody (rabbit polyclonal; ab97866, Abcam) and an anti-p63 antibody (mouse monoclonal; 4A4, Santa Cruz Biotechnology) were used. As the secondary antibodies, an Alexa Fluor (registered trademark) 488-conjugated anti-mouse IgG antibody, an Alexa Fluor 567-conjugated anti-rabbit IgG antibody, and an Alexa Fluor 647-conjugated anti-sheep IgG antibody (all from Invitrogen) were used. Each antibody was diluted with TBS containing 1% normal donkey serum and 0.3% Triton-X 100 before use. For nuclear staining, the cells were treated with 100-fold diluted Hoechst 33342 at room temperature for 10 minutes. For cell observation, Axio Observer.D1 (Carl Zeiss) was used. The results are shown in FIG. 3.

Neural crest cells can be defined as p75/SOX10-positive cells. At the 2nd week of culture, spherical forms of p75/SOX10-positive cells were detected on "511", and p75/SOX10-positive neural crest cells were detected on the other isoforms. In particular, expansion and migration of neural crest cells were promoted on "211". At the 4th week of culture, p75/SOX10-positive neural crest cells disappeared on "511" in the prior-art method, but p75/SOX10-positive neural crest cells were still detected on "211".

The expression of the neural cell marker TUBB3 was confirmed in the first and second zones of the control sample obtained on "511". TUBB3-positive cells on "111" and "211" formed fibers. The second zone on "411", which was positive for TUBB3, was expanded as compared with that on "511". No TUBB3-positive neural cells were observed on "332".

The expression of the neuroretinal marker CHX10 was confirmed in the second zone of the control sample obtained on "511", and CHX10-positive neuroretinal cells on "411" were greatly expanded. No neuroretina was observed on any other isoform. The expression of the epithelial marker E-cadherin was confirmed outside the 3rd zone of the control sample obtained on "511", and E-cadherin-positive epithelial cells on "332" were greatly expanded. A smaller number of E-cadherin-positive cells were observed on "111" and "211".

Corneal epithelial cells can be defined as PAX6/p63-positive cells. Differentiation into PAX6/p63-positive corneal epithelial cells was expanded on "332".

To summarize the above, "111" specifically promotes differentiation into neural cells, "211" specifically promotes differentiation into neural cells and neural crest cells, "332" specifically promotes differentiation into corneal epithelial cells and other epithelial cells, and "411" specifically promotes differentiation into retinal cells.

Example 3

Time-course Gene Expression Analysis in Differentiated Cells

Figure 4:
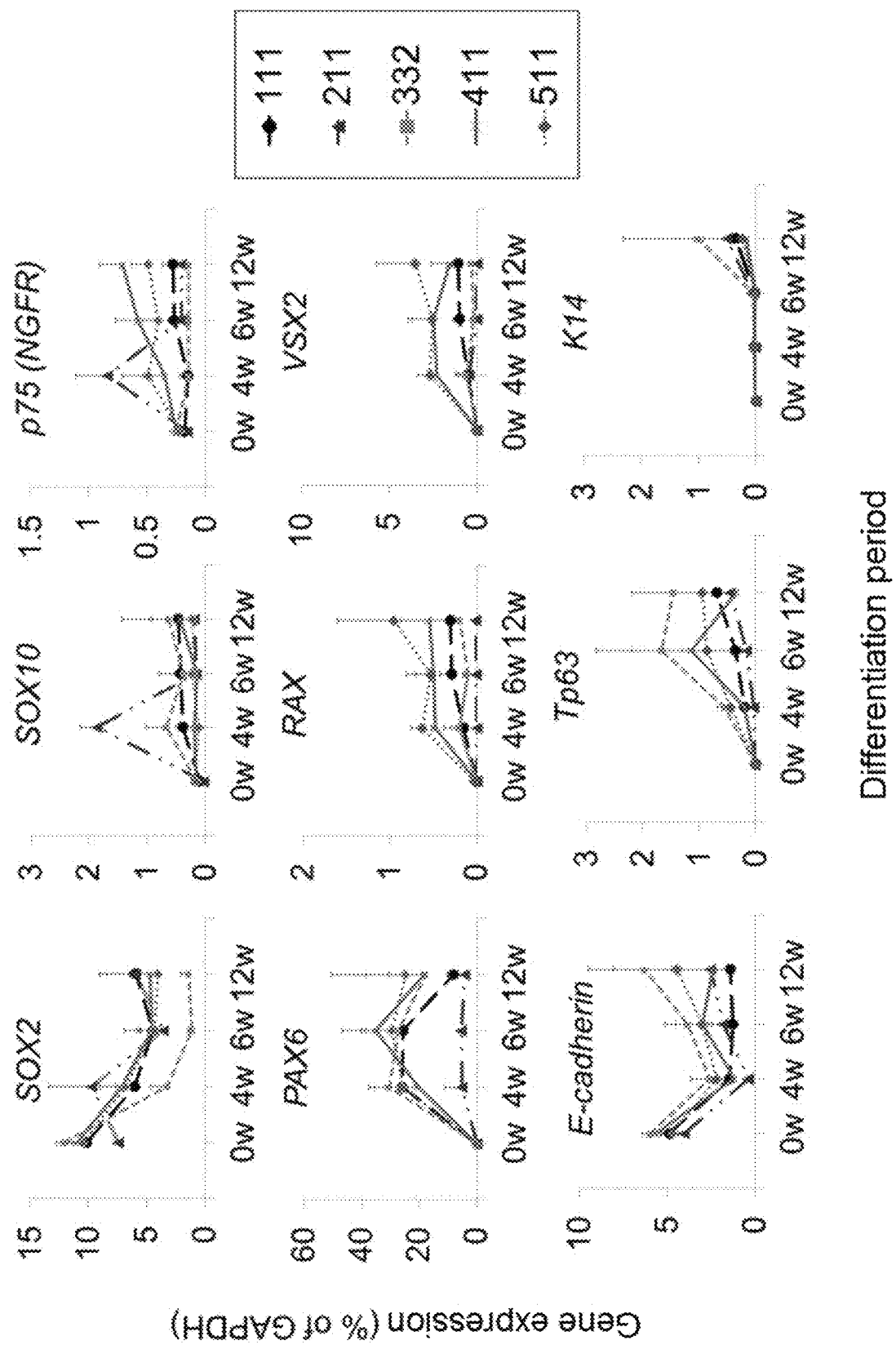
FIG. 4 shows the results of the time-course analysis of gene expression in iPS cell-derived differentiated cells.

Cell differentiation was induced as described in Example 1. Immediately before the start of differentiation culture (week 0), and after 4, 6 and 12 weeks, the medium was removed, followed by washing with PBS and subsequent treatment with QIAzol Lysis Reagent (QIAGEN). Reverse transcription was performed in the 20-µL reaction system with SuperScript (registered trademark) III First-Strand Synthesis SuperMix for qRT-PCR (Invitrogen). Using the prepared cDNA as a template, quantitative real-time PCR (qRT-PCR) was performed with ABI Prism 7500 Fast Sequence Detection System (Life Technologies). The results are shown in FIG. 4.

The gene expression of the neural marker SOX2 decreased in the cells differentiated on "332". The gene expression of the neural crest markers SOX10 and p75 increased in the cells differentiated on "211" at the fourth week, but the gene expression of PAX6, a major transcription factor in the eye was low. The gene expression of the retinal markers RAX and VSX2 was high in the cells differentiated on "411" and "511". The gene expression of the epithelial cell markers E-cadherin (Ecad), TP63 and K14 was high in the cells differentiated on "332". These results quantitatively agree with the qualitative results on isoform-directed differentiation in Example 2.

Example 4

Figure 5:
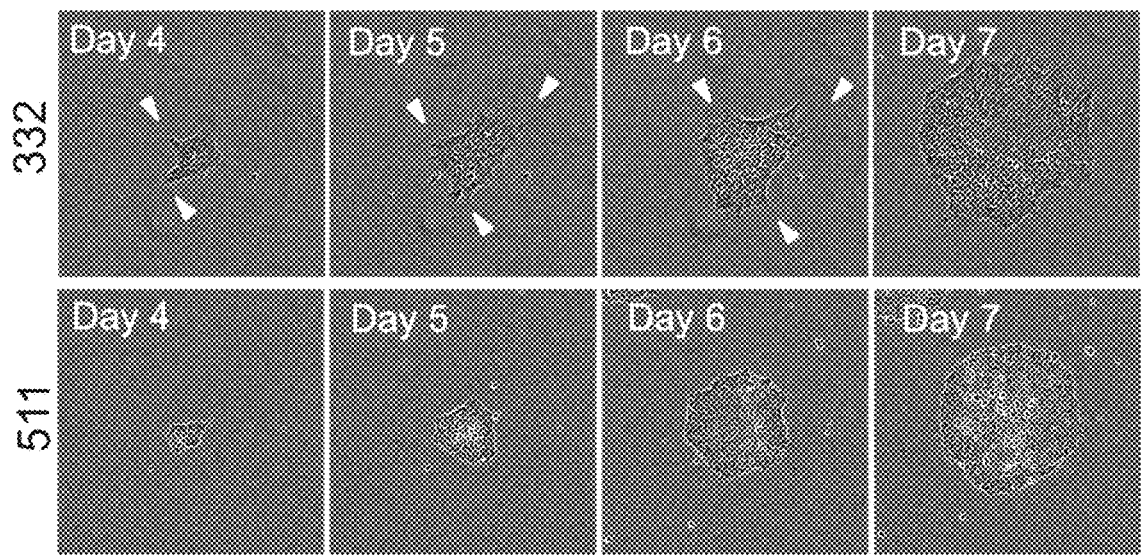
FIG. 5 shows the results of the time-lapse analysis in iPS cell colony formation.

Time-lapse Analysis of iPS Cell Colony Forming Process iPS cells were seeded on a culture vessel coated with "332" or "511" (0.5 µg/cm$^2$ for each isoform) and subjected to time-lapse recording using IncuCyte (registered trademark) Live Cell Analysis System (Essen BioScience) for acquisition of phase contrast images on the indicated culture days. The results are shown in FIG. 5.

When the iPS cells were cultured on "332", collective migration in a radial direction was frequently observed, and a colony spreading over a large area was formed. In contrast, when the iPS cells were cultured on "511", collective migration was hardly observed, and a high-density colony was formed.

Example 5

Figure 6:
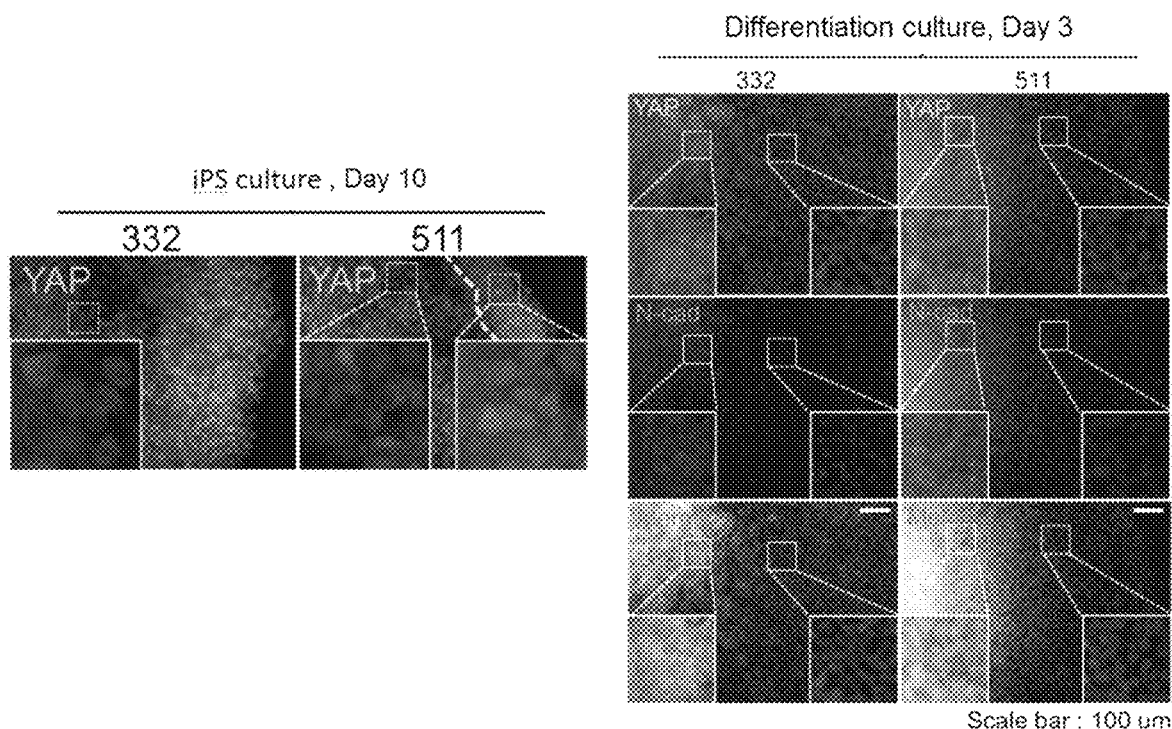
FIG. 6 shows the relation between the localization of the Hippo pathway-related transcription cofactor YAP in iPS cell colonies and neuroectodermal differentiation.

Relation between Localization of Hippo Pathway-related Transcription Cofactor YAP in iPS Cell Colonies and Neuroectodermal Differentiation iPS cells were seeded on a culture vessel coated with "332" or "511" (0.5 µg/cm$^2$ for each isoform) and cultured in StemFit (registered trademark) medium for 10 days (Ajinomoto). Separately, iPS cells seeded on a culture vessel coated with "332" or "511" (0.5 µg/cm$^2$ for each isoform) were cultured in StemFit (registered trademark) medium for 10 days and then cultured in the same differentiation medium (DM) as used in Example 1 for 3 days. After medium removal, the cells were washed with TBS and then fixed with 4% paraformaldehyde/PBS or cold methanol. After washing with TBS, the cells were permeabilized with 1% NST/TBS (1% normal donkey serum, 0.3% Triton-X 100) at 4° C. overnight. The cells were blocked with TBS containing 5% normal donkey serum and 0.3% Triton-X 100 at room temperature for 1 hour and then reacted with the primary antibody at room temperature for 1 hour or at 4° C. overnight. After 3 times of washing with PBS, the cells were reacted with the secondary antibody at room temperature for 1 hour. As the primary antibodies, an anti-YAP antibody (mouse monoclonal; 63.7, Santa Cruz Biotechnology) and an anti-N-cadherin antibody (rabbit monoclonal; EPR1791-4, Abcam) were used. As the secondary antibodies, an Alexa Fluor (registered trademark) 488-conjugated anti-mouse IgG antibody and an Alexa Fluor 594-conjugated anti-rabbit IgG antibody (both from Invitrogen) were used. Each antibody was diluted with 1% NST/TBS before use. For nuclear staining, the cells were treated with Hoechst 33342 at room temperature for 10minutes. For cell observation, Axio Observer.D1 (Carl Zeiss) was used. The results are shown in FIG. 6. The left panels show the results of YAP staining of the iPS cells after 10 days of culture. The right panels show the results of staining of the iPS cells after 3 days of differentiation culture. The top panel shows the results of YAP staining, the middle panel shows the results of N-cadherin staining, and the bottom panel shows showed a merged image of the top and middle panels.

When the iPS cells were cultured on "511", the colony periphery showed nuclear localization of YAP, while the highly-dense colony center showed extranuclear localization of YAP, which indicates Hippo signaling activation. After 3 days of culture in the differentiation medium, N-cadherin-positive cell differentiation, which indicates neuroectodermal differentiation, was observed only in the colony central region with extranuclear localization of YAP, that is, in the Hippo pathway-activated region. In contrast, the iPS cells cultured on "332" formed low-density colonies, resulting in nuclear localization of YAP, that is, Hippo pathway inactivation in the whole colony region. Thus, differentiation into N-cadherin-positive neuroectoderm was inhibited, while differentiation into surface ectodermal cells, which are progenitor cells of corneal epithelium, was promoted.

Example 6

Figure 7:
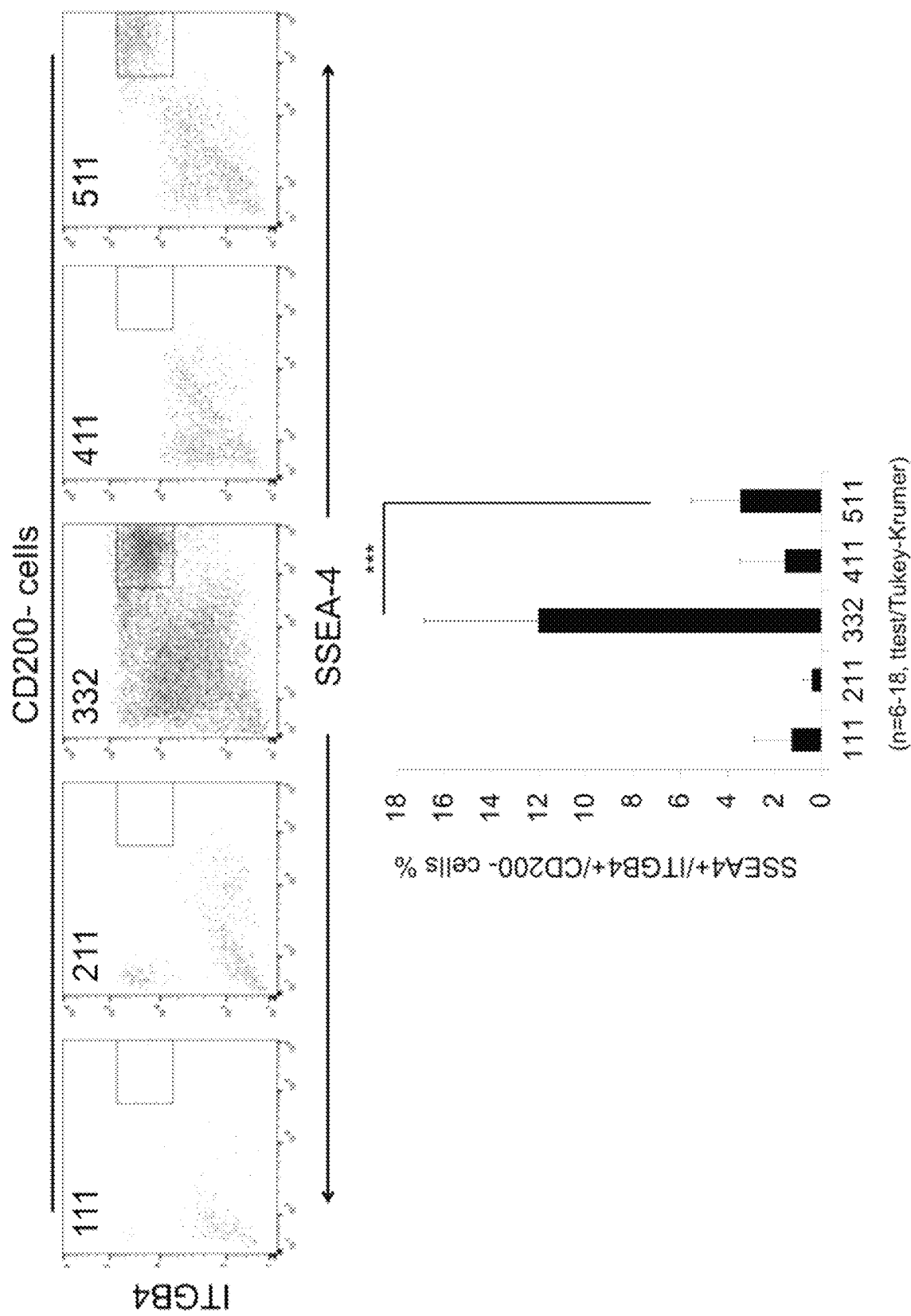
FIG. 7 shows the results of the analysis of corneal epithelial marker-positive rate in iPS cell-derived differentiated cells.

Analysis of Corneal Epithelial Marker-positive Rate in Differentiate Cells iPS cells were seeded on a culture vessel coated with "111", "211", "332", "411", or "511" (0.5 μg/cm$^2$ for each isoform) and differentiated as described in Example 1. The differentiated cells were treated with Accutase (Life Technologies) and resuspended in KCM medium (DMEM without glutamine/Nutrient Mixture F-12 Ham medium (3:1 (v/v), Life Technologies) supplemented with 5% FBS (Japan Bio Serum), 0.4 μg/mL hydrocortisone succinate (Wako), 2 nM 3,3', 5-triiodo-L-thyronine sodium salt (MP biomedicals), 1 nM cholera toxin (List Biological Laboratory), 2.25 μg/mL bovine transferrin HOLO form (Life Technologies), 2 mM L-glutamine, 0.5% insulin transferrin selenium solution (Life Technologies) and 1% penicillin-streptomycin). The cell suspension was filtered through a cell strainer (40 μm, BD Biosciences) and stained with an anti-SSEA-4 antibody (MC813-70, BioLegend), an anti-CD104 antibody (ITGB4; 58XB4, BioLegend or 624024, BD Pharmingen), and an anti-CD200 antibody (624052, BD Pharmingen) for 1 hour on ice. After washing with PBS, the stained cells were analyzed with cell sorter SH800 (SONY) or FACS Verse (BD Biosciences). For data analysis, FlowJo (Tree Star) was used. The results are shown in FIG. 7.

Corneal epithelial (progenitor) cells can be defined as SSEA4/ITGB4-positive cells as previously described in Non Patent Literature 1. The proportion of SSEA4/ITGB4-positive cells in the cells cultured on "332" was increased by about 3 times as compared with that in the cells cultured on "511". When the cells are cultured on "511", physical removal of the first and second zones by manual pipetting is required, but this procedure is cumbersome and susceptible to human error, which is a concern from the viewpoint of application to regenerative medicine. In contrast, when the cells are cultured on "332", the removal of non-epithelial cells by pipetting can be omitted, which is more advantageous.

Example 7

Gene Expression Analysis of Undifferentiation Marker in Differentiation Process and Evaluation of iPS Cell-derived Corneal Epithelial Cell Sheets after 6 Weeks of Differentiation iPS cells were seeded on a culture vessel coated with "332" or "511" (0.5 μg/cm$^2$ for each isoform) and differen-tiated as described in Example 1. The gene expression of the undifferentiation marker LIN28A in the cells after 4, 6 or 12 weeks of differentiation was analyzed as described in Example 3.

Figure 8:
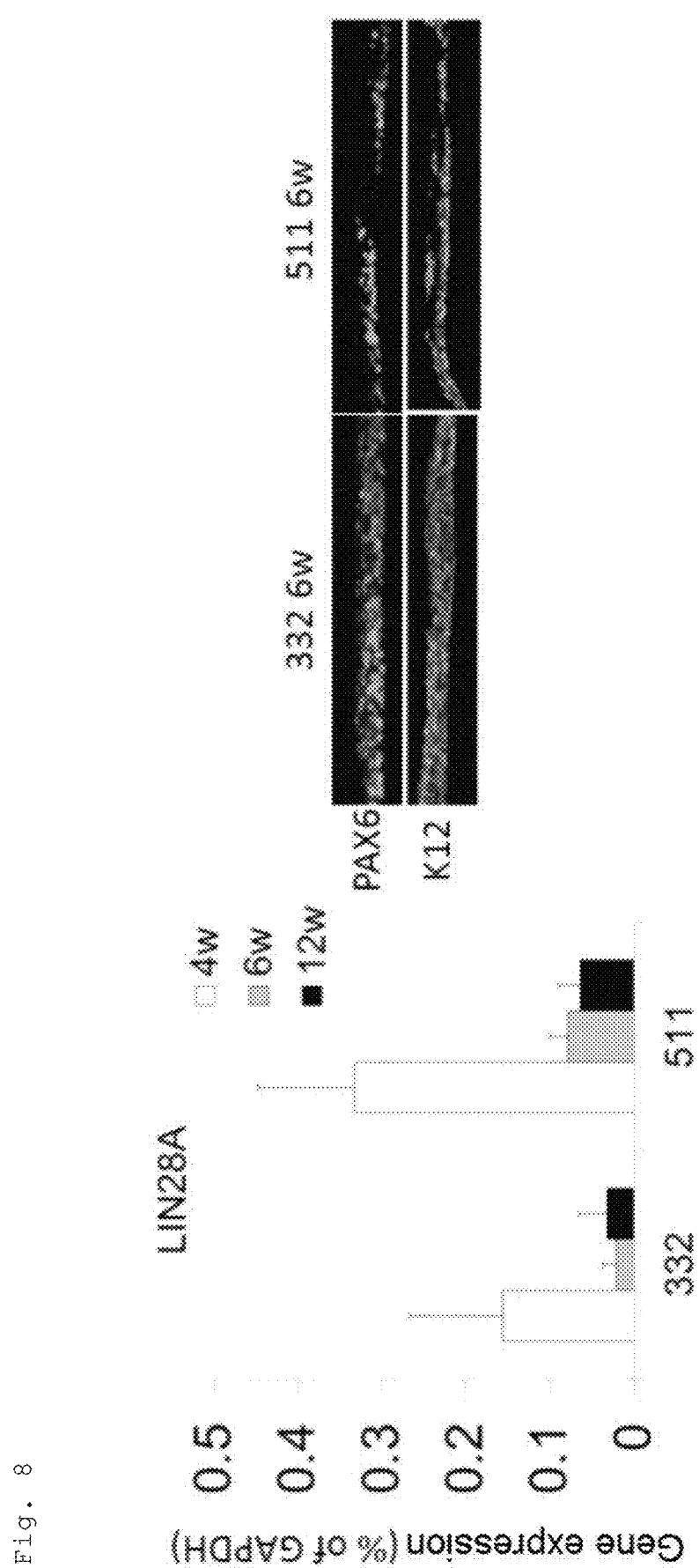
FIG. 8 shows the gene expression analysis of an undifferentiation marker in differentiation process and the cross-sections of iPS cell-derived corneal epithelial cell sheets after 6 weeks of differentiation.

Separately, the cells after 6 weeks of differentiation were stained with the antibodies as described in Example 6, and the cells positive for SSEA4 and ITGB4 as described in Non Patent Literature 1 were sorted out with cell sorter SH800 (SONY). The SSEA4/ITGB4-positive cells were seeded on cell culture inserts (BD Falcon) and cultured in CEM medium for 3 weeks. The cell sheet together with the underlying membrane was cut out with a scalpel, embedded in OCT compound, and frozen. Sections were prepared with a cryostat (Leica). The sections were air-dried, blocked with TBS containing 5% normal donkey serum and 0.3% Triton-X 100 at room temperature for 1 hour, and then reacted with the primary antibody at room temperature for 1 hour or at 4° C. overnight. After 3 times of washing with TBS, the cells were reacted with the secondary antibody at room temperature for 1 hour. As the primary antibodies, an anti-PAX6 antibody (rabbit polyclonal; ab97866, Abcam) and an anti-K12 antibody (goat polyclonal; N-16, Santa Cruz Biotechnology) were used. As the secondary antibodies, an Alexa Fluor (registered trademark) 488-conjugated anti-mouse IgG antibody and an Alexa Fluor 567-conjugated anti-rabbit IgG antibody (both from Invitrogen) were used. Each antibody was diluted with TBS containing 1% normal donkey serum and 0.3% Triton-X 100 before use. For nuclear staining, the cells were treated with 100-fold diluted Hoechst 33342 at room temperature for 10 minutes. For cell observation, Axio Observer.D1 (Carl Zeiss) was used. The results are shown in FIG. 8.

The use of iPS cell-derived differentiated cells raises the concern about tumorigenicity of contaminated undifferentiated cells from the viewpoint of clinical application. LIN28A is reportedly a useful marker for detection of contaminated undifferentiated cells. The expression level of the differentiation marker LIN28A in the cells cultured on "332" at any stage of differentiation was reduced by 2 times or more as compared with that in the cells cultured on "511". For the fabrication of corneal epithelial sheets, the usual procedure involves induced differentiation for about 12 weeks and subsequent isolation of only corneal epithelial cells by FACS. In this example, the sheet harvested after 6 weeks of differentiation on "511" insufficiently expressed the corneal epithelial markers PAX6 and K12, while the corneal epithelial sheet harvested after 6 weeks of differentiation on "332" sufficiently expressed both the markers. There results show that the use of "332" can reduce the differentiation period by half, i.e., to 6 weeks.

Example 8

Figure 9:
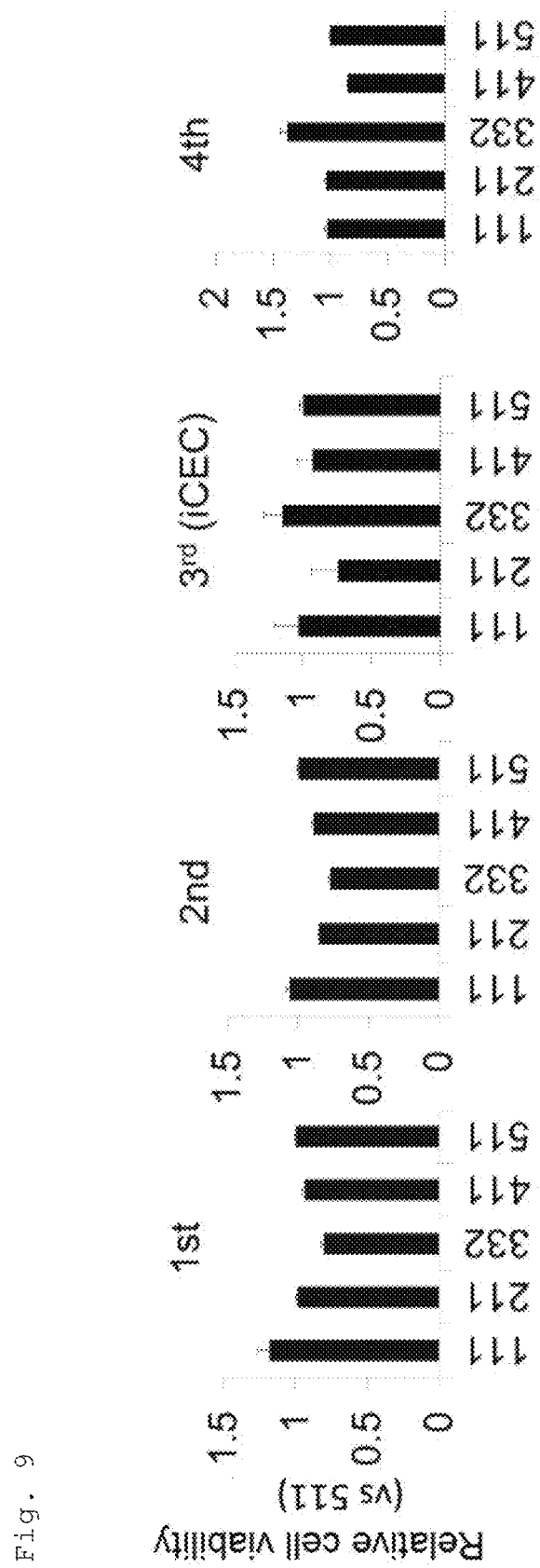
FIG. 9 shows the relative cell viability of eye-related cells in the SEAM structure formed by differentiation on various laminin isoforms.

Cell Viability of Eye-related Cells on Various Laminin Isoforms iPS cells were differentiated on "511" as described in Example 1, and the cells in the first to fourth zones in the SEAM structure after 6 weeks of differentiation were collected by manual pipetting. The cells in each zone were dissociated with StemPro (registered trademark) Accutase (registered trademark) (Thermo Fisher Scientific) or isolated by FACS sorting described in Example 7, and the same number of cells were seeded on cell culture plates coated with "111", "211", "332", "411", or "511" (0.5 μg/cm$^2$ for each isoform). After seeding, the cells were cultured in CDM medium for 6 weeks, the cell number was counted with Cell Counting Kit-8 (DOJINDO LABORATORIES), and the relative cell viability normalized to "511" was calculated. The results are shown in FIG. 9.

In the cells cultured on "332", zone 1 (nerve) cells and zone 2 (retina) cells were hardly grown, but zone 3 (corneal epithelium) cells and zone 4 (other epithelia) cells were grown. These results indicate that "332" specifically promotes the growth of the cells in zones 3 and 4 in the SEAM structure.

Example 9

Proportion of Differentiated Cells on Various Laminin Isoforms

Figure 10:
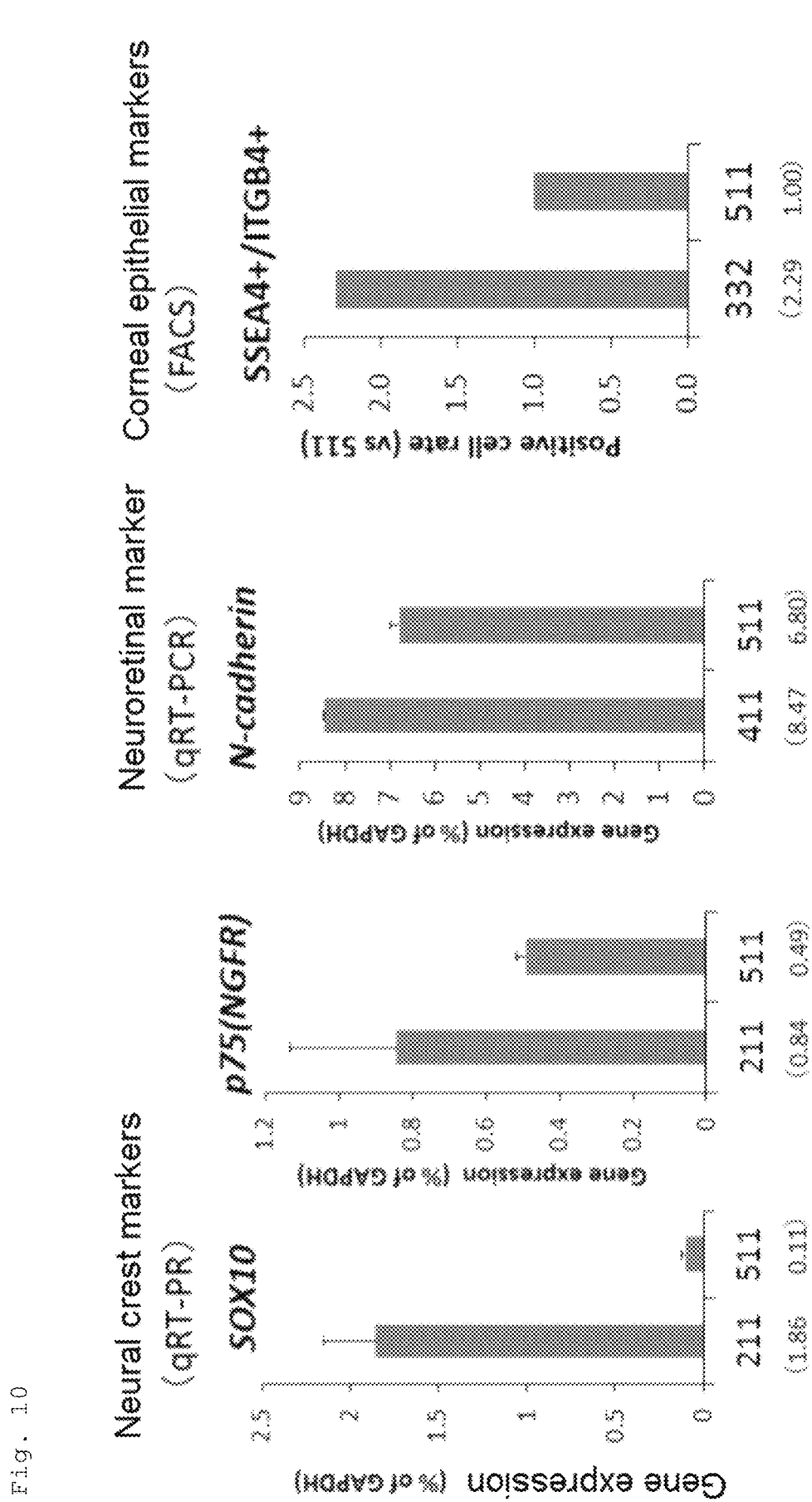
FIG. 10 shows the proportions of various differentiated cells in a cell population obtained by induced differentiation.

The gene expression in the differentiated cells was examined in Example 3. In this example, a detailed comparison of the expression levels was performed. More specifically, the data of neural crest marker gene expression in the cells differentiated on "211" and "511" at week 4 of differentiation were extracted. In addition, the analysis data of the N-cadherin gene expression in the cells differentiated on "411" and "511" at week 12 of differentiation were also extracted. Furthermore, the comparative data of the corneal epithelial marker-positive rate quantified in Example 6 were also extracted. The results are collectively shown in FIG. 10.

The gene expression levels of the neural crest markers SOX10 and p75 in the cells differentiated on "211" at week 4 of differentiation were about 17 times higher and about 2 times higher, respectively, than those in the cells differentiated on "511" at the same time point. As is already shown in FIG. 3, when the cells were cultured on "411", the expansion of the retinal region (CHX10-positive cells) was observed. In agreement with these results, the N-cadherin gene expression in the cells differentiated on "411" was about 1.25 times higher than that in the cells differentiated on "511", demonstrating that the proportion of retinal cells was higher than that of epithelial cells in the cells differentiated on "411". The proportion of the corneal epithelial marker-positive cells in the cells differentiated on "332" was 2 times or more higher than that in the cells differentiated on "511".

Example 10

Figure 11:
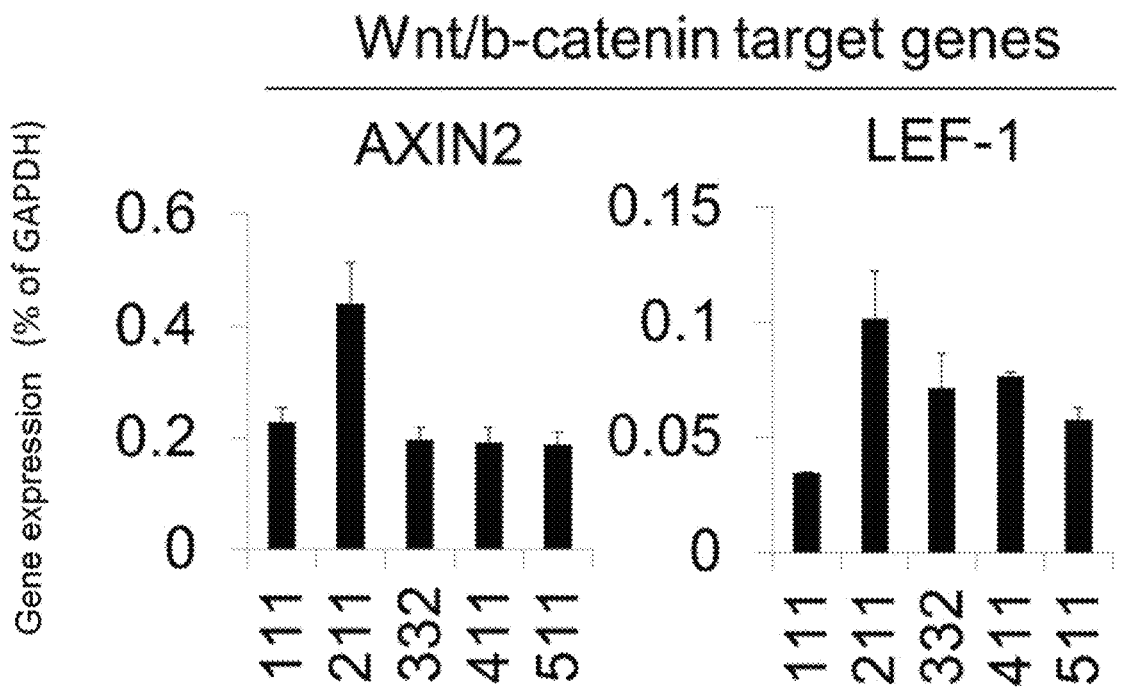
FIG. 11 shows the results of the expression analysis of Wnt signaling target genes in differentiated cells.

Expression Analysis of Wnt Signaling Target Genes iPS cells were seeded on a culture vessel coated with "111", "211", "332", "411", or "511" (0.5 μg/cm² for each isoform) and differentiated as described in Example 1. The expression of Wnt signaling target genes in the iPS cell-derived cells on day 3 of differentiation was analyzed. The results are shown in FIG. 11.

The gene expression of the Wnt signaling target genes AXIN2 and LEF-1 was upregulated in the cells differentiated on "211". These results indicate that Wnt signaling, which promotes neural crest differentiation, was activated in the cells differentiated on "211" as compared with the cells differentiated on other isoforms.

Example 11

Figure 12:
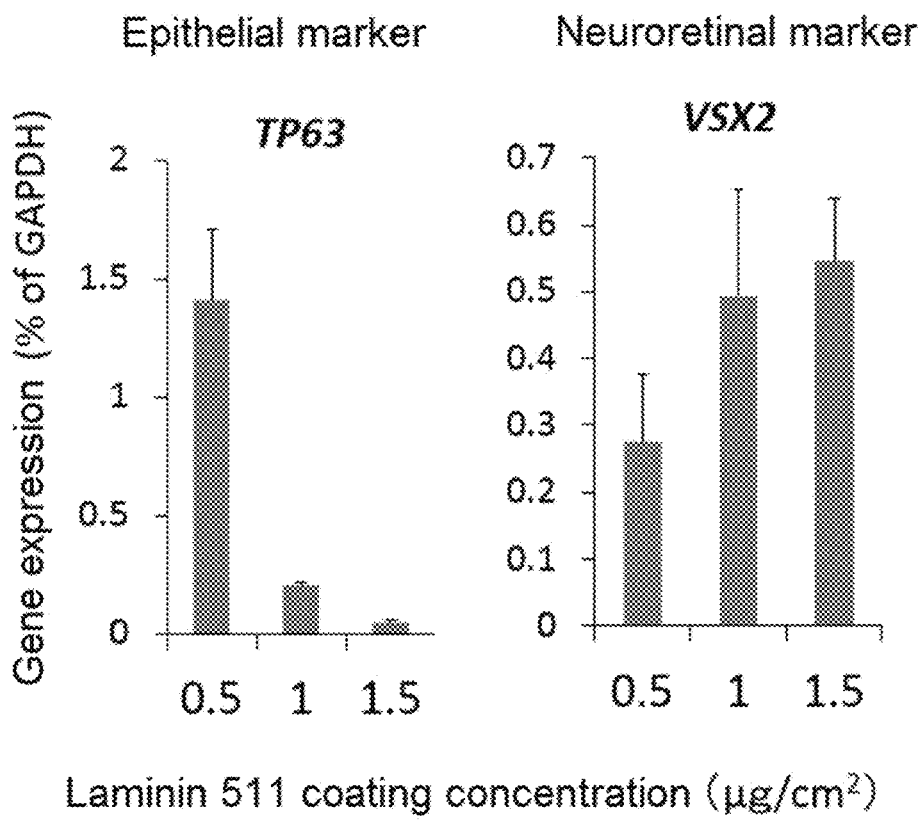
FIG. 12 shows differentiation control by laminin-coating concentration.

Differentiation Control by Laminin-coating Concentration iPS cells were differentiated on a culture vessel coated with "511" at 0.5, 1.0 or 1.5 μg/cm² as described in Example 1. The gene expression was analyzed after 12 weeks of differentiation. The results are shown in FIG. 12.

The gene expression of the stratified epithelial stem cell marker TP63 decreased in a "511" coating concentration-dependent manner, while the gene expression of the neuroretinal marker VSX2 increased in a "511" coating concentration-dependent manner. These results indicate that stronger interaction with iPS cells has more tendency to promote retinal differentiation while the moderate level of interaction promotes epithelization.

Example 12

Figure 13:
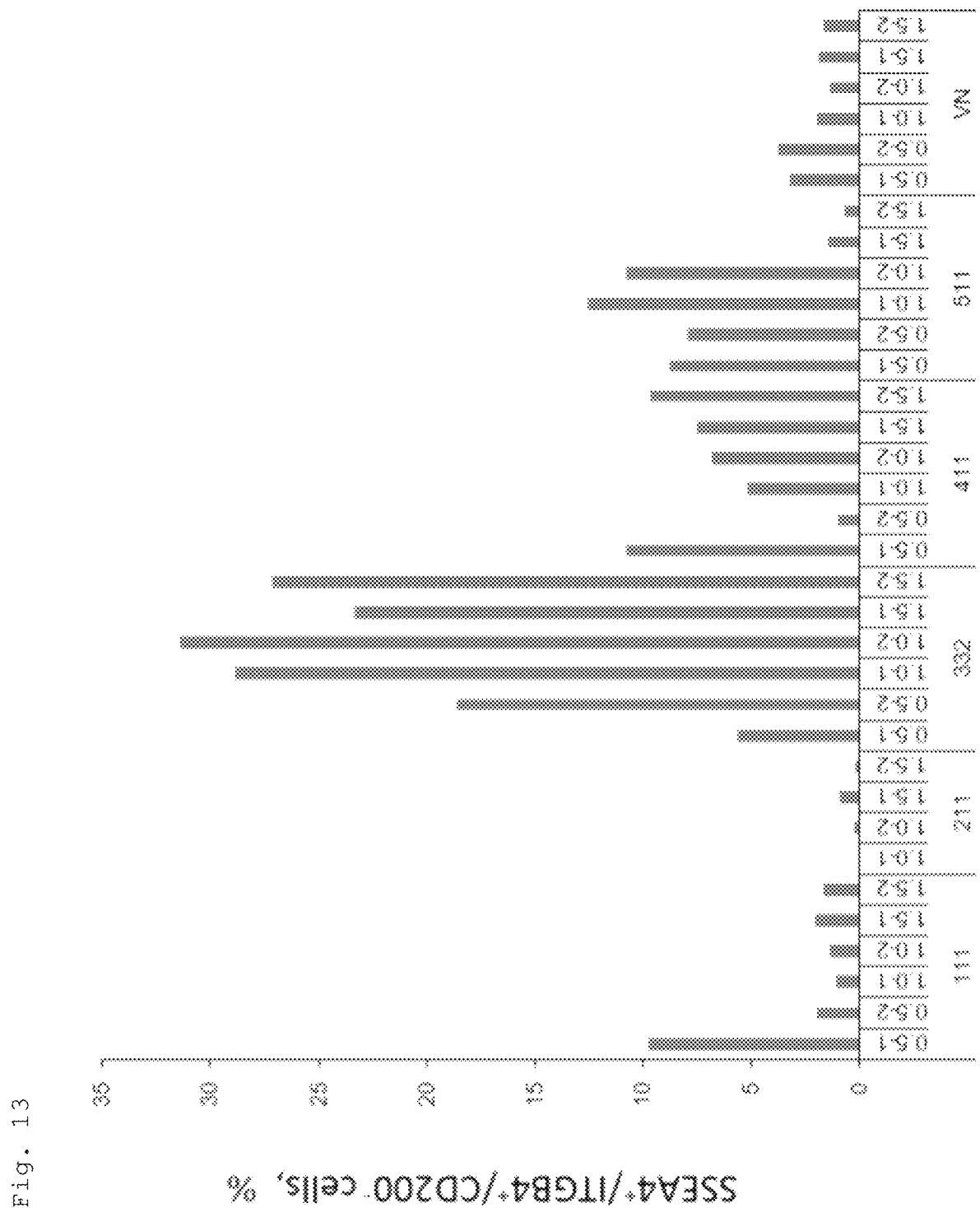
FIG. 13 shows the effect of the type and the coating concentration of the laminin on the efficiency of differentiation of iPS cells into corneal epithelial cells.

Induced Differentiation into Corneal Epithelial Cells on Various Laminin Isoforms at Different Coating Concentrations iPS cells were differentiated on a culture vessel coated with "111", "211", "332", "411", "511", or "VN" at 0.5, 1.0 or 1.5 μg/cm² as described in Example 1. The fraction of corneal epithelial cells was quantified by FACS analysis as described in Example 6. The results are shown in FIG. 13.

The cells cultured on "332" at each concentration were induced to differentiate into corneal epithelial cells in a stable and highly efficient manner. The differentiation efficiency of the cells cultured on "511" was reduced at higher concentrations.

Example 13

Figure 14:
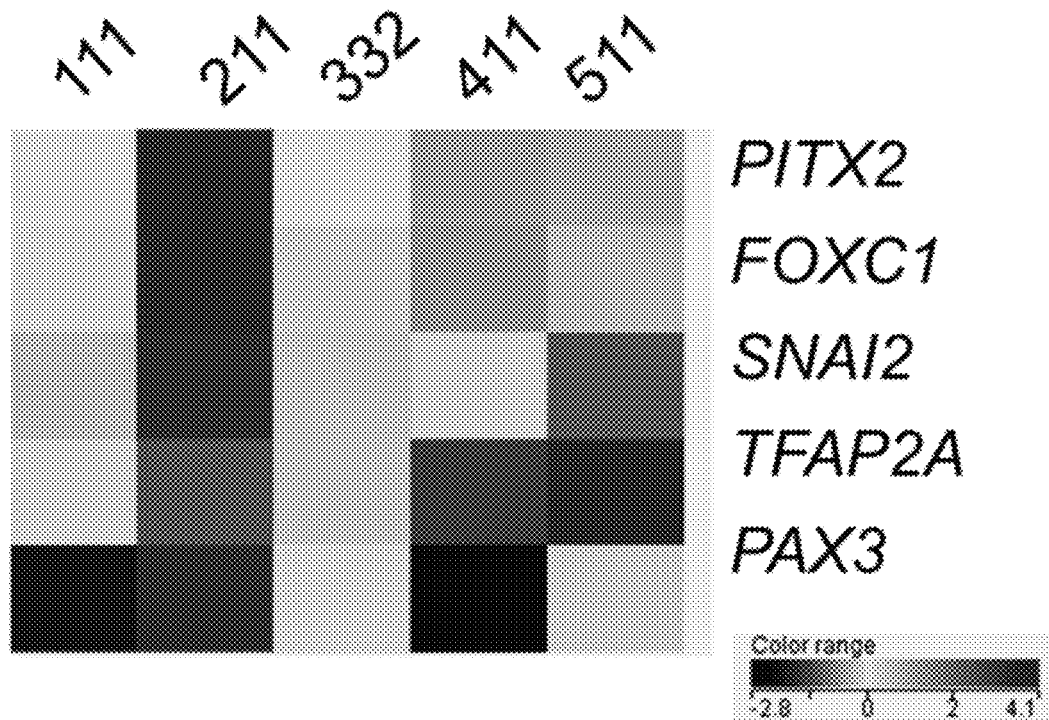
FIG. 14 shows the expression levels of neural crest cell marker genes in the differentiated cells on the indicated laminins.

Expression Analysis of Neural Crest Cell Marker Genes iPS cells were differentiated on a culture vessel coated with "111", "211", "332", "411", or "511" at 0.5 to 1.0 μg/cm² as described in Example 1. RNA was recovered from the iPS cell-derived cells on day 3 of differentiation according to the known method. The recovered RNA was purified with RNeasy Plus Micro Kit (Qiagen) and subjected to microarray analysis (Takara Bio) with SurePrint G3 human 8×60K slides (Agilent Technologies, Palo Alto, Calif., USA). The heatmap of neural crest cell marker genes was generated using GeneSpring GX software (Agilent Technologies). The results are shown in FIG. 14.

The cells differentiated on "211" showed high expression levels of the indicated neural crest markers, indicating that differentiation into neural crest cells can be well controlled using "211".

Example 14

Figure 15:
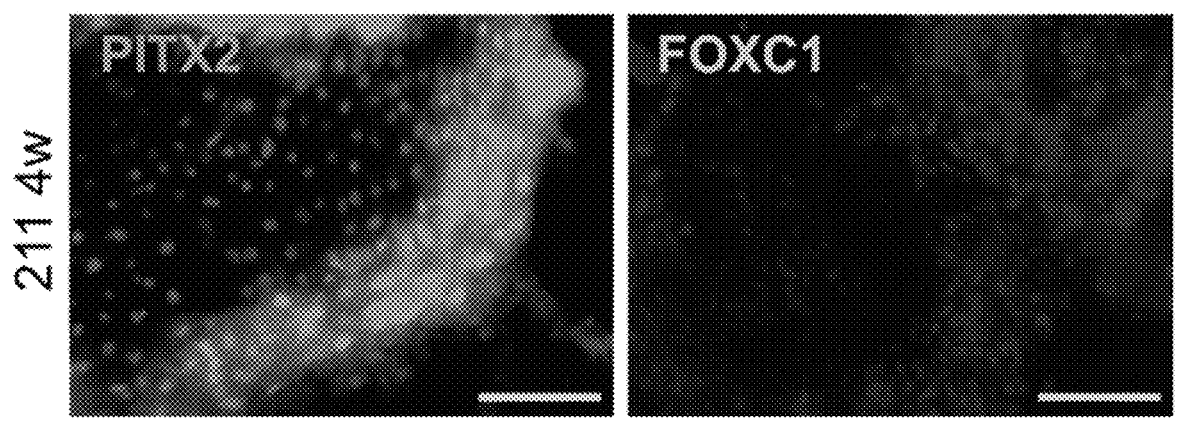
FIG. 15 shows the expression of eye-related neural crest cell markers in the cells differentiated on 211.

Expression Analysis of Neural Crest Cell Markers iPS cells were differentiated on a culture vessel coated with "211" at 0.5 to 1.0 μg/cm² as described in Example 1. The cells after 4 weeks of differentiation were reacted with antibodies as described in Example 2. As the primary antibodies, an anti-PITX2 antibody (Abcam, Ab55599) and an anti-FOXC1 antibody (Cell Signaling Technology, 8758) were used. As the secondary antibodies, an Alexa Fluor (registered trademark) 488-conjugated anti-mouse IgG antibody and an Alexa Fluor 594-conjugated anti-rabbit IgG antibody (both from Invitrogen) were used. Each antibody was diluted with 1% NST/TBS (1% normal donkey serum, 0.3% Triton-X 100) before use. Nuclear staining and cell observation were performed as described in Example 2. The results are shown in FIG. 15.

The cells positive for the eye-related neural crest markers PITX2 and FOXC1 were observed in the cells differentiated on "211".

Example 15

Figure 16:
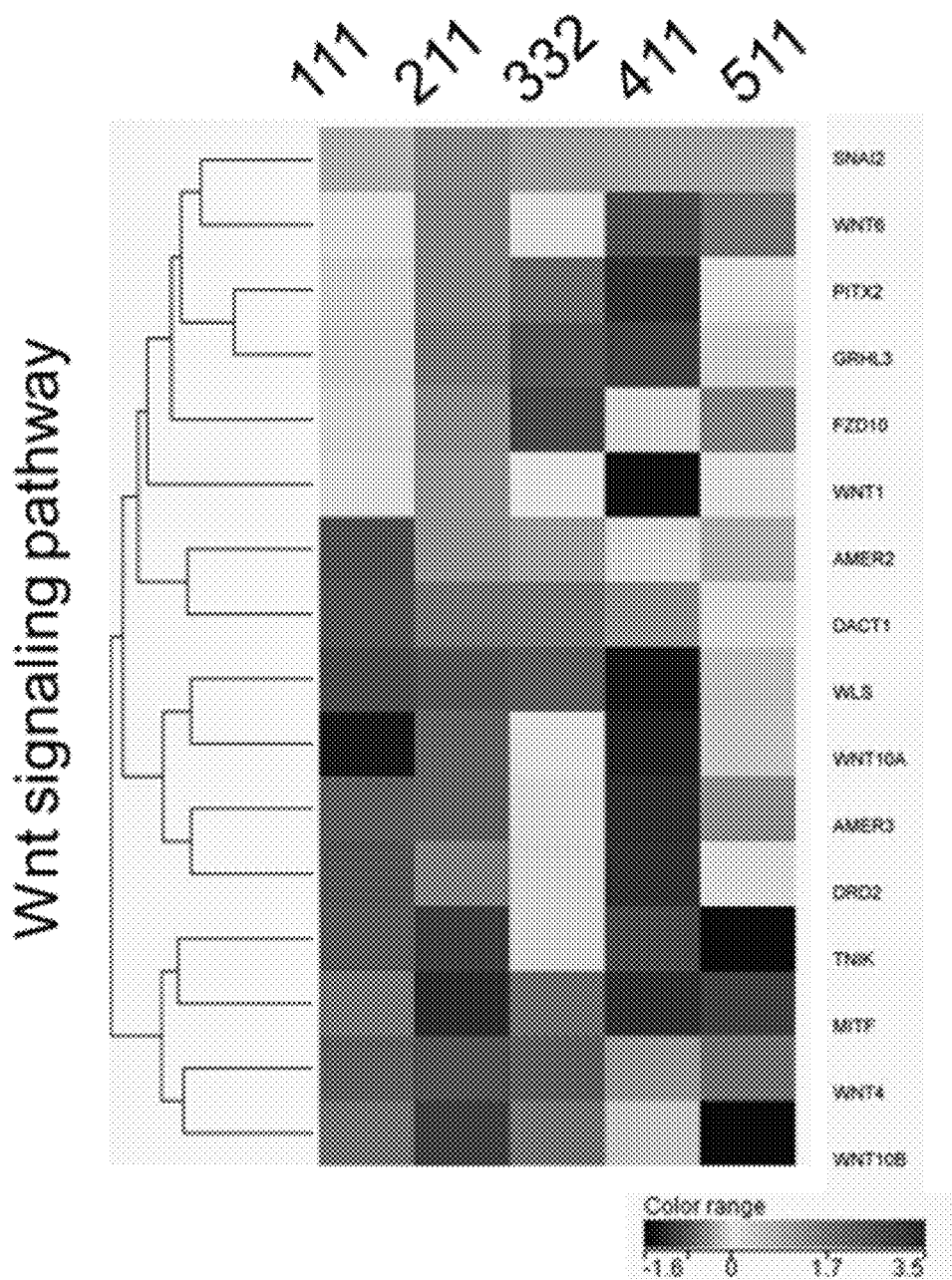
FIG. 16 shows the expression levels of Wnt signaling pathway-related genes in the cells differentiated on the indicated laminins.

Expression Analysis of Wnt Signaling Pathway-related Genes iPS cells were differentiated on a culture vessel coated with "111", "211", "332", "411", or "511", and the heatmap of the Wnt signaling pathway-related genes was generated as described in Example 13. The results are shown in FIG. 16.

The Wnt signaling pathway-related gene expression was upregulated in the cells differentiated on "211".

Example 16

Figure 17:
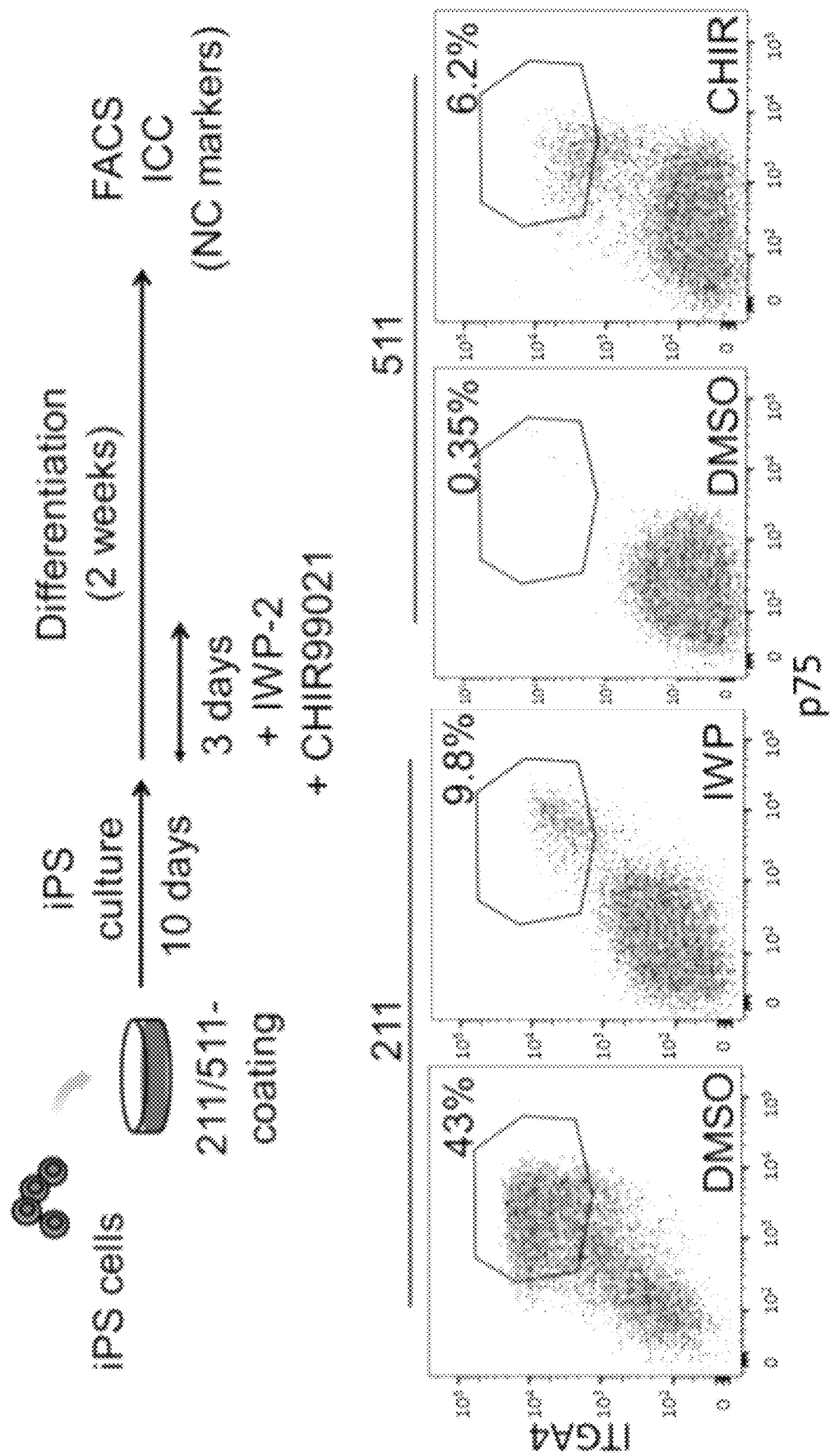
FIG. 17 shows the results of FACS analysis of the neural crest markers in the cells differentiated on laminin 211 or laminin 511 for 2 weeks during which treatment with the Wnt signaling activator or inhibitor had been performed for the first 3 days of differentiation.

Wnt Signaling and Neural Crest Cell Differentiation—Part 1 iPS cells were differentiated on a culture vessel coated with "211" at 1.0 µg/cm$^2$ or "511" at 0.5 µg/cm$^2$ as described in Example 1. The cells were treated with the Wnt signaling pathway inhibitor IWP-2 or the Wnt signaling pathway activator CHIR99021 for the first 3 days of differentiation. After 2 weeks of differentiation, FACS analysis was performed as described in Example 6. For FACS analysis, antibodies against CD271 (p75, C40-1457; BD Pharmingen, Franklin Lakes, N.J., USA) and CD40d (ITGA4, 9F10; BioLegend) were used. Only DMSO was added for the controls. The results are shown in FIG. 17. A schematic representation of the differentiation process in this example is shown in the upper half of the figure.

A high proportion (43%) of neural crest cells were observed in the cells differentiated on "211". However, addition of the Wnt inhibitor inhibited neural crest cell differentiation on "211". The proportion of neural crest cells in the cells differentiated on "511" was as low as 0.35% but was increased to 6.2% by the Wnt activator treatment. Therefore, the Wnt signaling pathway is shown to be a key to neural crest cell differentiation.

Example 17

Wnt Signaling and Neural Crest Cell Differentiation—Part 2

Figure 18:
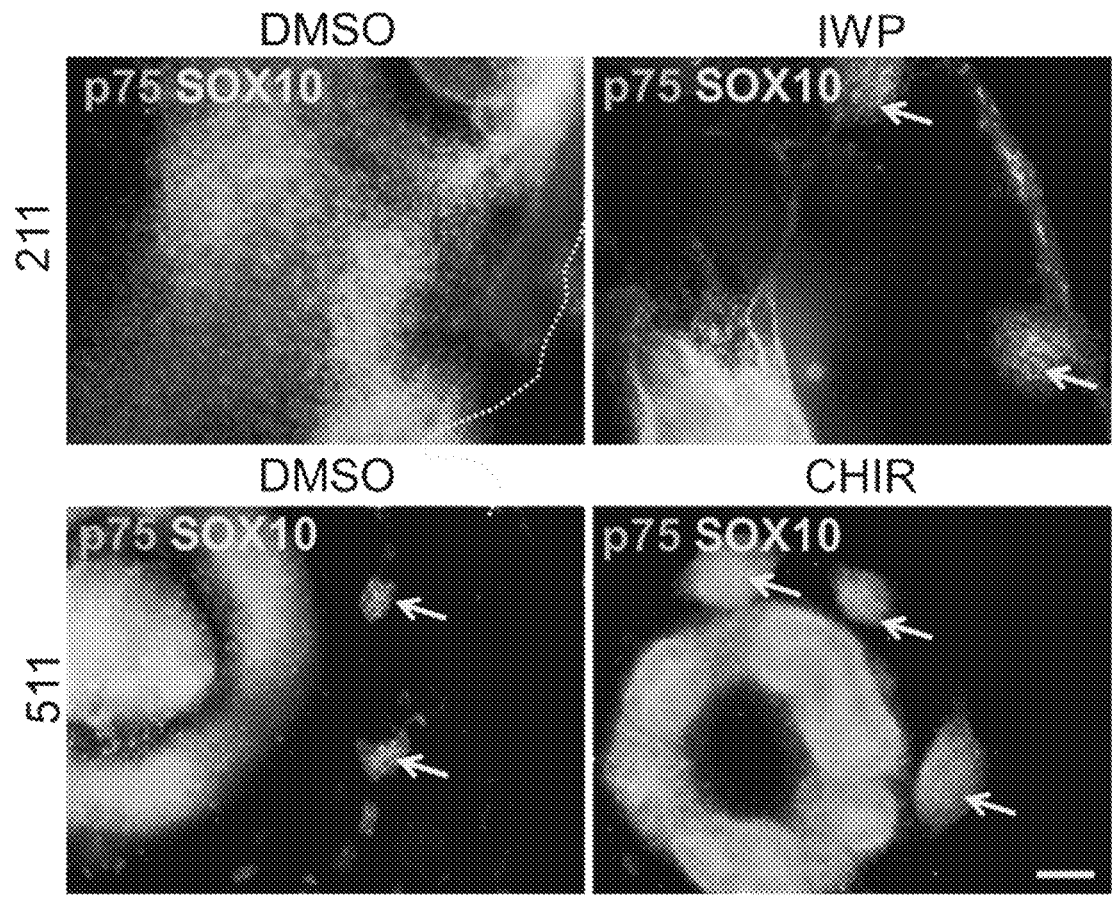
FIG. 18 shows the results of immunostaining to examine the effect of the Wnt signaling pathway on differentiation into neural crest cells on laminin 211 or laminin 511.

The cells differentiated in Example 16 were immunostained as described in Example 2 with an anti-p75 antibody (ADVANCED TRGETING SYSTEMS, AB-N07) and an anti-SOX10 antibody (Santa Cruz Biotechnology, sc-17342). The results are shown in FIG. 18.

Neural crest cells positive for p75 and SOX10 were observed in the cells differentiated on "211" (DMSO), but Wnt inhibition reduces the proportion of p75/SOX10 positive cells (IWP). In contrast, the emergence of neural crest cells positive for p75 and SOX10 on "511" was promoted by Wnt activation (shown by the comparison of DMSO and CHIR). The arrows represent neural crest cells positive for p75 and SOX10.

Example 18

Figure 19:
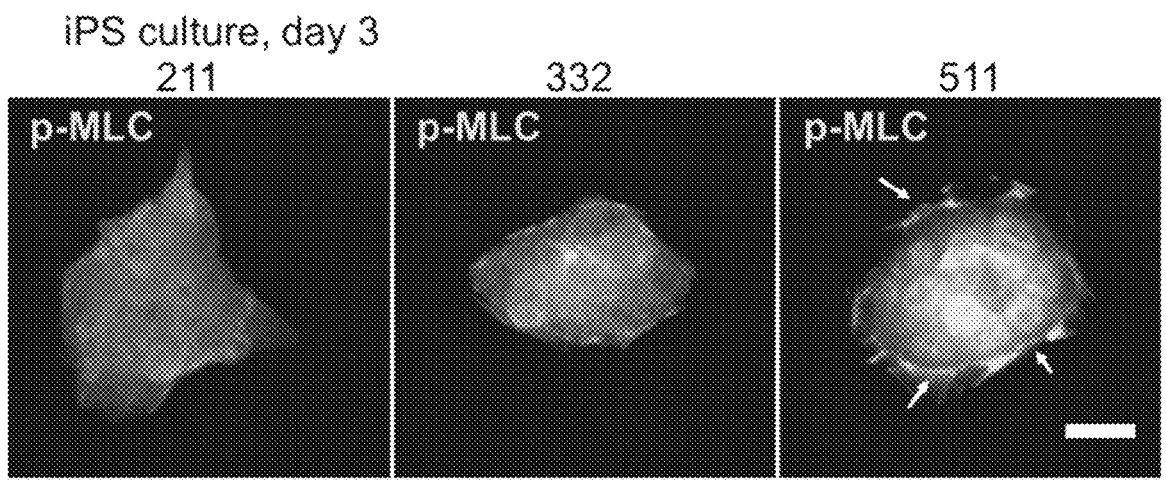
FIG. 19 shows the results of the examination of the effect of the indicated laminins on phosphorylated MLC localization in iPS cell colonies.

Analysis of MLC (Myosin Light Chain) Phosphorylation iPS cells were cultured on a culture vessel coated with "211" at 1.0 µg/cm$^2$, "332" at 0.5 µg/cm$^2$, or "511" at 0.5 µg/cm$^2$ as described in Example 1. After 3 days of culture, the cells were fixed and then immunostained with an anti-myosin light chain (phospo S20) antibody (Abcam, ab2480) as described in Example 2. The results are shown in FIG. 19.

MLC phosphorylation was observed (arrows in the figure) at the periphery of the iPS cell colony on "511", indicating contraction at the colony periphery. In contrast, weak contraction was observed at the periphery of the iPS cell colony on laminin "211".

Example 19

Figure 20:
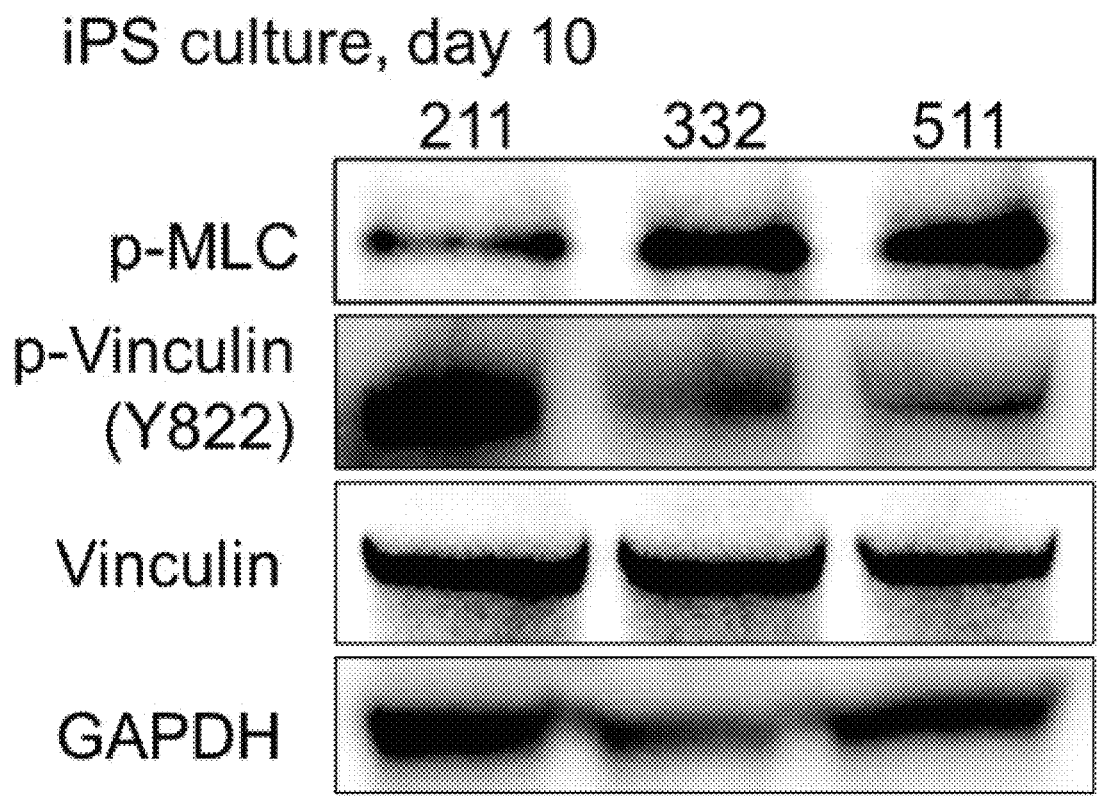
FIG. 20 shows the results of the examination of the effect of the indicated laminins on the expression level of phosphorylated MLC and cell-cell interaction in iPS cell colonies.

Analysis of Phosphorylation of MLC and Vinculin iPS cells were cultured as described in Example 18 for 10 days and lysed in RIPA buffer (Thermo). Protein concentrations were determined with Pierce (registered trademark) BCA Protein Assay Kit (Thermo Fisher Scientific), and equal amounts of protein were subjected to SDS-PAGE. After SDS-PAGE, the proteins were transferred to a membrane using iBlot system (Invitrogen, Waltham, Mass., USA). The membrane was reacted with a primary antibody against p-MLC (ab2480, 1:1000; Abcam, Cambridge, UK), p-vinculin (V4889, 1:1,000; Sigma-Aldrich), vinculin (ab18058; Abcam), or GAPDH (ab8245, 1:5,000; Abcam). The membrane was then reacted with a secondary antibody against horseradish peroxidase-conjugated anti-mouse IgG (ab6789, 1:5,000; Abcam) or anti-rabbit IgG (ab97051, 1:5,000; Abcam). The proteins were detected with ECL Prime reagent (GE Healthcare, Little Chalfont, UK) and scanned with ChemiDoc XRS+ imaging system (Bio-Rad, Hercules, Calif., USA). The results are shown in FIG. 20.

The cells cultured on "511" showed a strong phosphorylation of MLC, while the cells cultured on "211" showed a weak phosphorylation of MLC. In contrast, phosphorylation of vinculin at Y822, which recognizes cell-cell adhesion, was particularly strong in the cells cultured on "211" (J Cell Biol. 2014 Apr 28;205(2):251-63. doi: 10.1083/jcb.201309092. Epub 2014 Apr 21.). These results show that strong contraction in the iPS cells cultured on "511" and predominant cell-cell adhesion in the iPS cells cultured on "211".

Example 20

Figure 21:
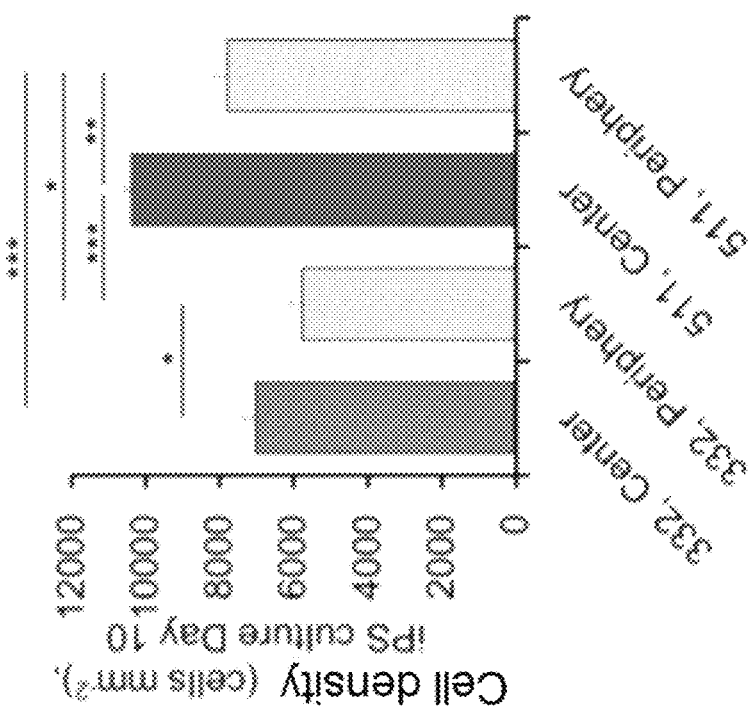
FIG. 21 shows the results of the examination of the effect of the indicated laminins on the central and peripheral cell density of iPS cell colonies.
Figure 21:
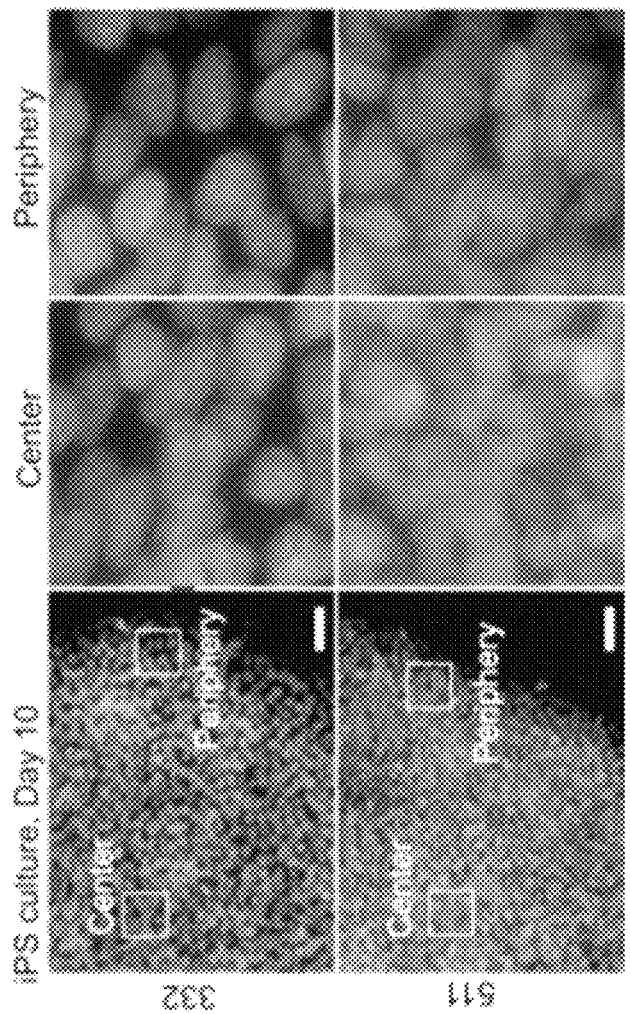

Cell Density in iPS Colonies iPS cells were cultured on a culture vessel coated with "332" at 0.5 µg/cm$^2$ or "511" at 0.5 µg/cm$^2$ as described in Example 1. After 10 days of culture, blocking and nuclear staining were performed as described in Example 2. The cell number was counted, and the cell density per mm$^2$ was calculated. The results are shown in FIG. 21.

The cell density was the highest at the center of the iPS colony on "511".

Example 21

Figure 22:
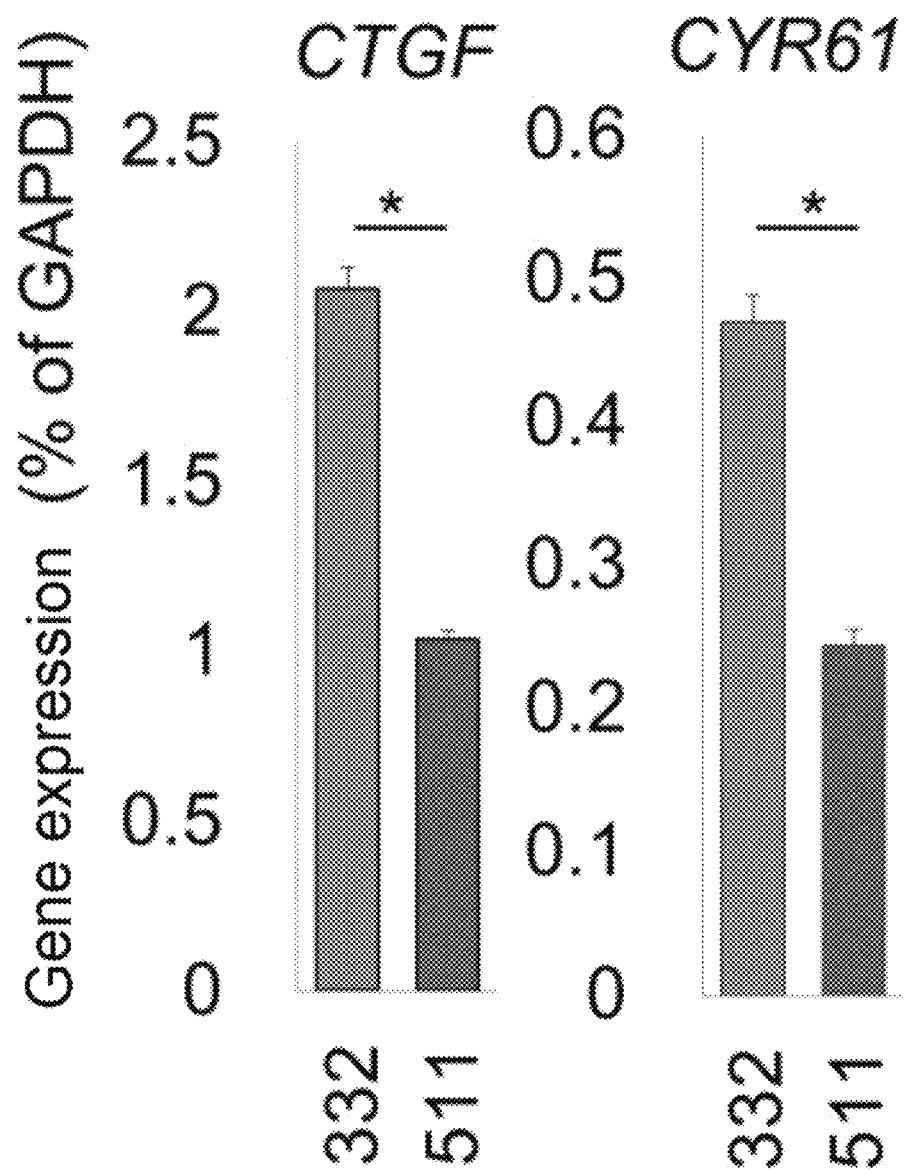
FIG. 22 shows the results of the examination of the effect of the indicated laminins on YAP activity in the iPS cells.

Difference in YAP Activity iPS cells were cultured on a culture vessel coated with "332" at 0.5 µg/cm$^2$ or "511" at 0.5 µg/cm$^2$ as described in Example 1. After 10 days of culture, gene expression was analyzed as described in Example 3. The results are shown in FIG. 22.

The iPS cells cultured on "511" showed lower expression levels of YAP target genes (CTGF, CYR61) as compared with those in the iPS cells cultured on "332", indicating that YAP activity was inhibited in the iPS cells cultured on "511".

Example 22

Figure 23:
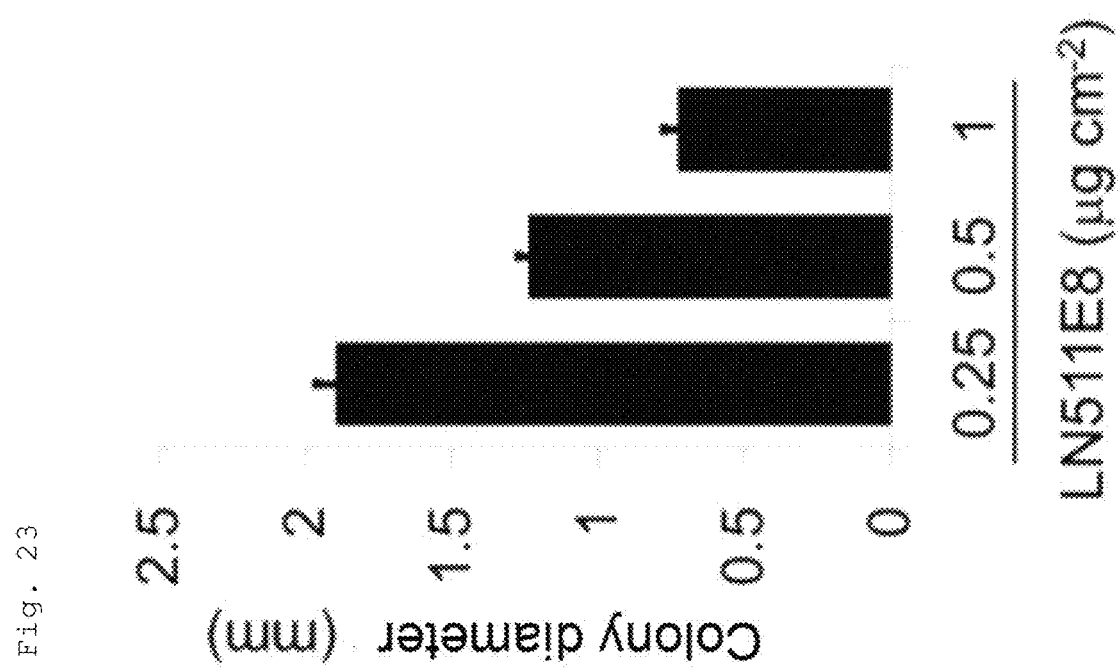
FIG. 23 shows the results of the examination of the relation of iPS cell colony compaction and neuroectodermal differentiation at different concentrations of the laminin.

Colony Compaction and Neuroectodermal Differentiation iPS cells were cultured on a culture vessel coated with "511" at 0.25 to 1 µg/cm$^2$ as described in Example 1. After 10 days of culture, the diameters of colonies were quantified with EVOS FL Auto system (Life Technologies). Separately, the iPS cells after 10 days of culture were subjected to 3 days of differentiation culture and then immunostained as described in Example 2. The results are shown in FIG. 23.

iPS cell colonies became more compact in a "511" coating concentration-dependent manner. Along with such colony compaction, the PAX6 expression increased in a coating concentration-dependent manner. These results show that "511" promotes colony compaction and neuroectodermal differentiation.

Example 23

Figure 24:
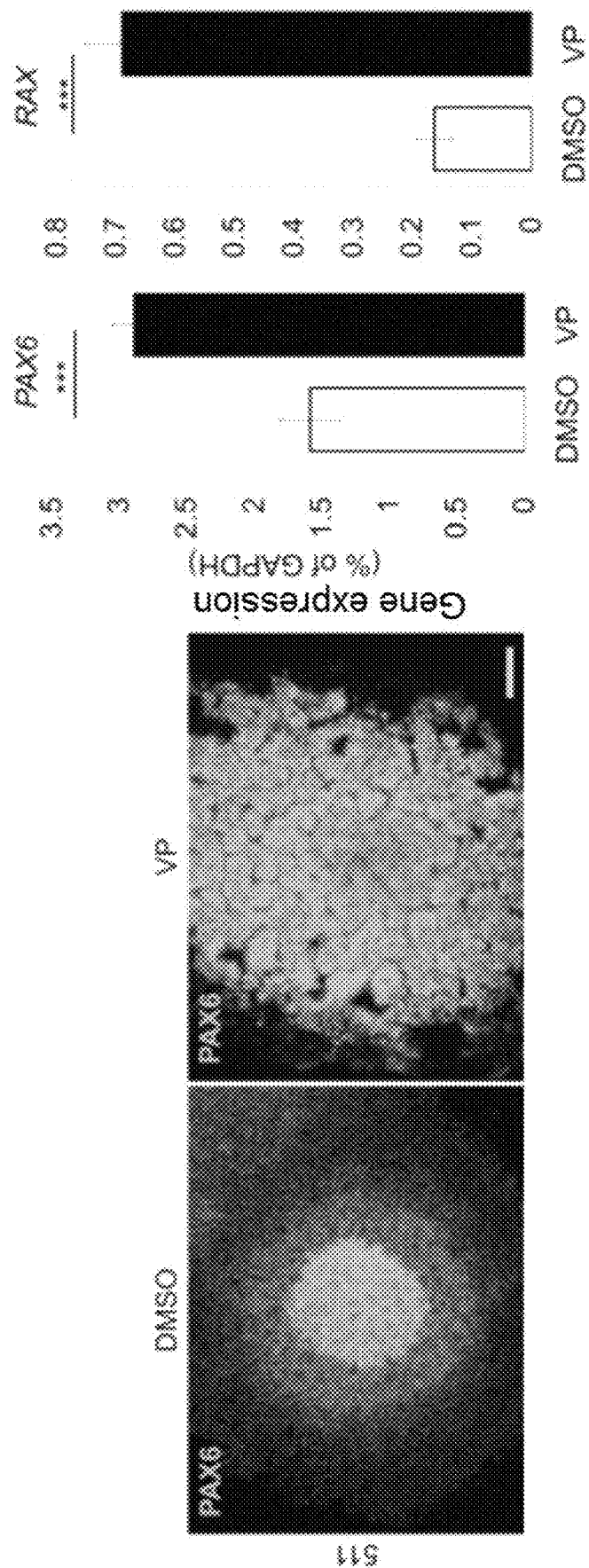
FIG. 24 shows the results of the examination of the relation of YAP transcription activity in iPS cell colonies and neuroectodermal differentiation.

YAP Activation and Neuroectodermal Differentiation iPS cells were cultured on a culture vessel coated with "511" at 0.5 µg/cm$^2$ as described in Example 1. After 10 days of culture, the cells were cultured for 3 days in the differentiation medium supplemented with verteporfin (VP) or DMSO and then immunostained with an anti-PAX6 antibody (BioLegend, PRB-278P) as described in Example 2. In addition, gene expression was analyzed as described in Example 21. The results are shown in FIG. 24.

The expression of neuroectodermal markers, such as PAX6 and RAX, was increased by the treatment with VP, a YAP-TEAD inhibitor. That is, the inactivation of YAP at the early stage of differentiation was shown to promote neuroectodermal differentiation. These results show that "511" promotes iPS colony compaction, increases cell density, and promotes YAP inactivation and subsequent neuroectodermal differentiation.

INDUSTRIAL APPLICABILITY

According to the present invention, a cell population containing any desired proportion of differentiated cells can be produced from pluripotent stem cells in a simple manner. The cell population obtained by this production method is very useful for cell therapy-based treatment strategies for diseases.

The invention claimed is:

1. A method for producing corneal epithelial cells, the method comprising differentiating human iPS cells to corneal epithelial cells by:
   (a) culturing said human iPS cells in a culture medium in contact with a laminin 332E8 fragment to generate a first cell population that has been contacted with said laminin332E8 fragment;
   (b) culturing said first cell population in a serum free medium in contact with a laminin 332E8 fragment to generate a second cell population;
   (c) culturing said second cell population of differentiated cells in a corneal differentiation medium, which lacks epidermal growth factor (EGF) or fibroblast growth factor 2 (FGF2) but comprises keratinocyte growth factor (KGF) in contact with a laminin 332E8 fragment to produce a third cell population; and
   (d) culturing said third cell population of differentiated cells in a corneal epithelial cell maintenance medium, which comprises keratinocyte growth factor (KGF) in contact with a laminin 332E8 fragment to produce corneal epithelial cells.

2. The method of claim 1 further comprising detecting the presence of a marker for corneal epithelial cells with the corneal epithelial cells produced by said method.

3. The method of claim 2, wherein the marker is E-cadherin, TP63, PAX6, K12, K14, or SSEA4/ITGB4.

4. The method of claim 1 further comprising:
   (e) isolating the corneal epithelial cells produced by the method;
   (f) seeding 1×10$^5$ or more of said corneal epithelial cells isolated in step (e) on a plate, and
   (g) culturing the seeded cells of step (f) on the plate to confluency to form a corneal epithelial cell sheet.

5. The method of claim 4, wherein the corneal epithelial cells are isolated by FACS.

6. The method of claim 1, wherein steps (a), (b), (c) and (d) are performed in a vessel coated with said laminin332E8 fragment.

7. The method of claim 1, wherein steps (a), (b), (c) and (d) are performed by contacting said iPS cells with a carrier comprising said laminin332E8 fragment.

8. The method of claim 1, wherein the concentration of said laminin332E8 fragment used in said method is about 0.25-2.0 µg/cm$^2$.

9. The method of claim 1, wherein step (a) is performed for 8-10 days.

10. The method of claim 1, wherein step (b) is performed for 4 weeks.

11. The method of claim 1, wherein step (c) is performed for 4 weeks.

12. The method of claim 1, wherein step (d) is performed for 2-5 weeks.

13. The method of claim 1, further comprising analyzing for the presence or absence of a marker indicating the presence of an undifferentiated populations of cells in the corneal epithelial cells produced by said method.

14. The method of claim 13, wherein said marker is LIN28A.

* * * * *